United States Patent [19]
Zheng et al.

[11] Patent Number: 5,856,351
[45] Date of Patent: Jan. 5, 1999

[54] ARTEMISININ DIMER COMPOUNDS HAVING ANTICANCER ACTIVITY

[76] Inventors: Qun Y. Zheng, 1263 S. Elmoro Ct., Superior, Colo. 80027; Lynn G. Darbie, 1621 Firerock Ct., Loveland, Colo. 80538

[21] Appl. No.: 887,708

[22] Filed: Jul. 3, 1997

Related U.S. Application Data

[63] Continuation of Ser. No. 496,771, Jun. 29, 1995, Pat. No. 5,677,468.
[51] Int. Cl.$^6$ .................................................. A61K 31/335
[52] U.S. Cl. ............................................................ 514/450
[58] Field of Search ............................................. 514/450

[56] References Cited

U.S. PATENT DOCUMENTS 5,225,437  7/1993  Posner et al. ........................... 514/450

OTHER PUBLICATIONS

"Synthesis of a Novel Ring Contracted Artemisinin Derivative," *Bioorganic & Medicinal Chemistry Letters* 4(5)751–752 (1994).

"Qinghaosu (Artemisinin): An Antimalarial Drug from China,", D.L. Klayman, *Science* 228:1049–1055 (May 1985).

"Cytotoxicity of Artemisinin–Related Endoperoxides to Ehrlich Ascites Tumor Cells," *Journal of Natural Products*, 56(6): 849–856 (Jun. 1993).

"Artemisinin (Qinghaosu): A New Type of Antimalarial Drug," *Department of Chemistry*, University of St. Andrews, Scotland, Anthony R. Butler.; Chemical Society Reviews (1992), pp. 85–90.

"Exradorinarily Potent Antimalarial Compounds: New, Structurally Simple, Easily Synthesized, Tricyclic 1,2,4–Trioxanes," *Journal of Medicinal Chemistry* vol. 35, No. 13, (1992).

"Artemisinin," *The Royal Society of Tropical Medicine and Hygiene*, vol. 88 Supplement 1 (Jun. 1994).

Screening Date Summary NSC 369397, National Cancer Institute Report, Jan. 5, 1995.

*Primary Examiner*—Laura L. Stockton
*Attorney, Agent, or Firm*—Chrisman, Bynum & Johnson; Steven C. Petersen

[57] ABSTRACT

Novel artemisinin dimers of structure

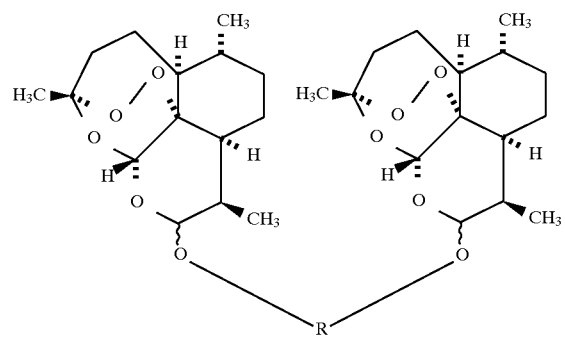

which possess anticancer activity.

22 Claims, 18 Drawing Sheets

ARTEMISININ DIMER COMPOUNDS HAVING ANTICANCER ACTIVITY

This application is a continuation of application Ser. No. 08/496,771, filed Jun. 29, 1995 now U.S. Pat. No. 5,679,468.

BACKGROUND OF THE INVENTION

1. Field of the Invention

The present invention relates to a novel class of artemisinin dimers which demonstrate useful anticancer activity.

2. Description of the State of Art

*Artemisia annua L.*, also known as qing hao or sweet wormwood, is a pervasive weed that has been used for many centuries in Chinese traditional medicine as a treatment for fever and malaria. Its earliest mention, for use in hemorrhoids, occurs in the *Recipes for 52 Kinds of Diseases* found in the Mawangdui Han dynasty tomb dating from 168 B.C. Nearly five hundred years later Ge Hong wrote the Zhou Hou Bei Ji Fang Handbook of Prescriptions for Emergency Treatments) in which he advised that a water extract of qing hao was effective at reducing fevers. In 1596, Li Shizhen, the famous herbalist, wrote that chills and fever of malaria can be combated by qing hao preparations. Finally, in 1971, Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage.

Artemisinin (3,6,9-trimethyl-9,10b-epidioxyperhydropyranol [4,3,2-jk]benzoxepin-2-one) is a member of the amorphane subgroup of cadinenes and has the following structure (I).

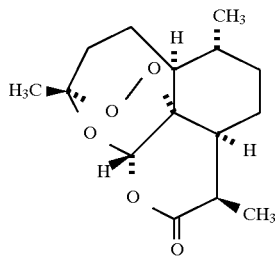

Artemisinin or QHS was the subject of a 1979 study conducted by the Qinghaosu Antimalarial Coordinating Research Group involving the treatment of 2099 cases of malaria (*Plasmodium vivax* and *Plasmodium falciparum* in a ratio of about 3:1) with different dosage forms of QHS, leading to the clinical cure of all patients. See, Qinghaosu Antimalarial Coordinating Research Group, *Chin. Med. J.*, 92:811 (1979). Since that time QHS has been used successfully in several thousand malaria patients throughout the world including those infected with both chloroquine-sensitive and chloroquine-resistant strains of *P. falciparum*. Assay of QHS against *P. falciparum*, in vitro, revealed that its potency is comparable to that of chloroquine in two Hanian strains (Z. Ye, et al., J. Trad. Chin. Med., 3:95 (1983)) and of mefloquine in the Camp (chloroquine-susceptible) and Smith (chloroquine-resistant) strains, D. L. Klayman, et al., *J. Nat. Prod.*, 47:715 (1984).

Most research suggests that QHS acts by an oxidative mechanism and it effects changes in both red blood cells and in the limiting and other membranes of the malarial parasite. At concentrations much higher than those used clinically, QHS affects red blood cell deformability in a manner which suggests that QHS acts as an efficient prooxidant, M. D. Scott, et al., *J. Lab. Clin. Med.*, 114:40 (1989). At even higher concentrations QHS brings about complete lysis of red blood cells, G. Haoming, *Zhongguo Yaoli Xuebao*, 7:269 (1986). The mechanism of action of QHS appears to involve two steps, S. Meshnick, *Transactions of the Royal Society of Tropical Medicine and Hygiene* 88(1): S1/31–S1/32, (1994). In the first step, activation, intra-parasite iron catalyzes the cleavage of the endoperoxide bridge and the generation of free radicals. A free radical is a short-lived and highly reactive molecule that contains an unpaired electron. In the second step, alkylation, the QHS-derived free radical forms covalent bonds with parasitic proteins which leads to alternations in ribosomal organization and the endoplasmic reticulum. Nuclear membrane blebbing develops followed by segregation of the nucleoplasm. The parasite continues to undergo degenerative changes with disorganization and death occurring from eight hours onwards following the initial exposure to QHS.

Although QHS is effective at suppressing the parasitemias of *P. vivax* and *P. falciparum*, the problems encountered with recrudescence, and the compounds solubility, due to the lactone ring in QHS, led scientists to modify QHS chemically, a difficult task because of the chemical reactivity of the peroxide linkage which is an essential moiety for antimalarial activity.

Reduction of QHS in the presence of sodium borohydride results in the production of dihydroartemesinin (II-1) or DHQHS, (illustrated in structure II below), in which the lactone group is converted to a lactol hemiacetal) function, with properties similar to QHS. QHS in methanol is reduced with sodium borohydride to an equilibrium mixture of α- and β-isomers of dihydroartemisinin. The yield under controlled conditions is 79% (QHS, 0.85M with $NaBH_4$ 6.34M. 7.5 equivalents in methanol, 12 L at 0°–5° C. for about 3 hours followed by quenching to neutrality at 0°–5° C. and dilution with water to precipitate dihydroartemisinin), A. Brossi, et al., *Journal of Medicinal Chemistry*, 31:645–650 (1988). Using DHQHS as a starting compound a large number of other derivatives, such as,

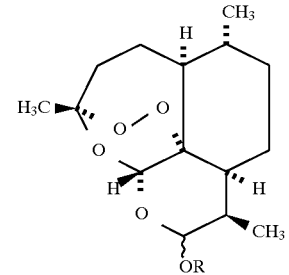

1  R = H

2  R = $CH_3$

3  R = $CH_2CH_3$

4  R = $COCH_2CH_2COONa$

5  R = $CH_2C_6H_4COOH$

6  R = $CH_2CC_6H_4COONa$

7  R =

-continued

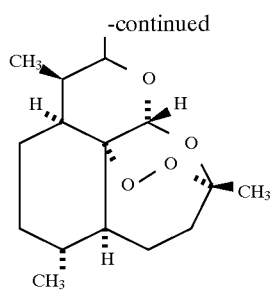

artemether (compound II-2), arteether (II-3), sodium artesunate (II-4), artelinic acid (II-5), sodium artelinate (II-6), DHQHS condensation by-product (II-7) and the olefinic compound, structure III,

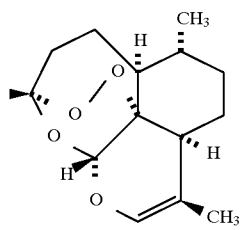

III have been produced.

Artemether (II-2) is produced by reacting β-DHQHS with boron trifluoride ($BF_3$) etherate or HCl methanol:benzene (1:2) at room temperature. A mixture of β- and α-artemether (70:30) is obtained, from which the former is isolated by column chromatography and recrystallized from hexane or methanol, R. Hynes, *Transactions of the Royal Society of Tropical Medicines and Hygiene*, 88(1): S1/23–S1/26 (1994). For arteether (II-3), (Brossi, et al., 1988), the α-isomer is equilibrated (epimerized) to the β-isomer in methanol:benzene mixture containing $BF_3$ etherate. Treatment of DHQHS with an unspecified dehydrating agent yields both the olefinic compound, (III), and the DHQHS condensation by-product (II-7), formed on addition of DHQHS to (III), M. Cao, et al., *Chem. Abstr.*, 100:34720k (1984). Until recently, the secondary hydroxy group in DHQHS (1I-1) provided the only site in an active QHS related compound that had been used for derivatization. See B. Venugopalan "Synthesis of a Novel Ring Contracted Artemisinin Derivative," *Bioorganic & Medicinal Chemistry Letters*, 4(5):751–752 (1994).

The potency of various QHS-derivatives in comparison to QHS as a function of the concentration at which the parasitemia is 90 percent suppressed ($SD_{50}$) was recently reported by D. L. Klayman, "Qinghaosu (Artemisinin): An Antimalarial Drug from China," *Science* 228:1049–1055 (1985). Dr. Klayman found that the olefinic compound III is inactive against *P. bergher*-infected mice, whereas, the DHQHS condensation by-product (II-7) has an $SD_{50}$ of 10 mg/Kg in *P. bergher*-infected mice. Thus, the DHQHS ether dimer proved to be less potent than QHS, which has an $SD_{50}$ of 6.20 mg/Kg. Following, in order of their overall antimalarial efficacy, are the three types of derivatives of DHQHS (II-1) that have been produced: (QHS)<ethers (II, R=alkyl) <esters [II, R=C(=O)-alkyl or -aryl]<carbonates [II, R=C (=O)O-alkyl or -aryl].

Over the past twenty years only a few drugs isolated from higher plants have yielded clinical agents, the outstanding examples being vinblastine and vincristine from the Madagascan periwinkle, *Catharanthus roseus*, etoposide, the semi-synthetic lignam, from May-apple *Podophyllum peltatum* and the diterpenoid taxol, commonly referred to as paclitaxel, from the Pacific yew, *Taxus brevifolia*. Of these agents, paclitaxel is the most exciting, recently receiving approval by the Food and Drug Administration for the treatment of refractory ovarian cancer. Since the isolation of QHS, there has been a concerted effort by investigators to study other therapeutic applications of QHS and its derivatives.

National Institutes of Health reported that QHS is inactive against P388 leukemia. See NCI Report on NSC 369397 (tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that QHS displays very little anticancer activity. A series of artemisinin-related endoperoxides were tested for cytoxicity to Ehrlich ascites tumor (EAT) cells using the microculture tetrazolum (MTT) assay, H. J. Woerdenbag, et al. "Cytotoxicity of Artemisinin-Related Endoperoxides to Ehrlich Ascites Tumor Cells," *Journal of Natural Products*, 56(6):849–856 (1993). The MTT assay, used to test the artemisinin-related endoperoxides for cytoxicity, is based on the metabolic reduction of soluble tetrazolium salts into insoluble colored formazan products by mitochondrial dehydrogenase activity of the tumor cells. As parameters for cytoxicity, the $IC_{50}$ and $IC_{80}$ values, the drug concentrations causing respectively 50% and 80% growth inhibition of the tumor cells, were used. QHS (I), had an $IC_{50}$ value of 29.8 μM. Derivatives of DHQHS (II-1) being developed as antimalarial drugs (artemether (II-2), arteether (III-3), sodium artesunate (II-4), artelinic acid (II-5) and sodium artelinate (II-6)), exhibited a somewhat more potent cytoxicity. Their $IC_{50}$ values ranged from 12.2 μM to 19.9 μM. The DHQHS condensation by-product (II-7), disclosed previously by M. Cao, et al., 1984, was the most potent cytotoxic agent, its $IC_{50}$ being 1.4 μM. At this drug concentration, the condensation by-product (II-7) is approximately twenty-two times more cytoxic than QHS and sixty times more cytotoxic than DHQHS (II-1), the parent compound.

There is still a need, therefore, for developing structural analogs of QHS as antitumor agents that have potency equivalent to or greater than known anticancer agents.

SUMMARY OF THE INVENTION

Accordingly, it is an object of this invention to provide a class of artemisinin dimers which demonstrate antitumor activity.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the compositions of this invention comprise artemisinin dimers, of the following structure, having anticancer activity;

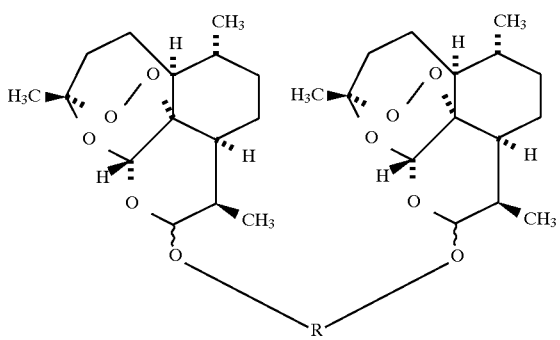

where R is a linker such as a bivalent aromatic, arylene, lower alkylene, lower alkenylene, bivalent halide species, a bivalent protein, an atom or —CH$_2$CH$_2$—(XCH$_2$CH$_2$)$_n$— where X is O, S or NY where Y is H or alkyl, and n is 0–20 or R is —X—Z—X— where X is a bivalent ester, carbamate or carbonate species and Z is a bivalent aromatic, arylene, polyethylene glycol, lower alkylene, lower alkenylene or bivalent halide compound.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In all of the following drawings the horizontal axis depicts various dilutions of the test compound, ranging from $10^{-4}$ to $10^{-9}$ molar, that were exposed to the specified cancer cell lines. The vertical axis (percentage growth) depicts the growth of the specified cancer cell line when exposed to a specific concentration of the tested compound as compared to the growth of the same cancer cell line not exposed to any compound.

In the Drawings:

FIG. 1a depicts the dose response curves generated by exposing various leukemia cancer cell lines to various concentrations of QHS.

FIG. 1b depicts the dose response curves generated by exposing various leukemia cancer cell lines to various concentrations of the β, β-QHS PEG dimer of the present invention.

FIG. 1c depicts the dose response curves generated by exposing various leukemia cancer cell lines to various concentrations of the α, β-QHS PEG dimer of the present invention.

FIG. 1d depicts the dose response curves generated by exposing various leukemia cancer cell lines to various concentrations of paclitaxel.

FIG. 2a depicts the dose response curves generated by exposing various non-small cell lung cancer cell lines to various concentrations of QHS.

FIG. 2b depicts the dose response curves generated by exposing various non-small cell lung cancer cell lines to various concentrations of the β, β-QHS PEG dimer of the present invention.

FIG. 2c depicts the dose response curves generated by exposing various non-small cell lung cancer cell lines to various concentrations of the α, β-QHS PEG dimer of the present invention.

FIG. 2d depicts the dose response curves generated by exposing various non-small cell lung cancer cell lines to various concentrations of paclitaxel.

FIG. 3a depicts the dose response curves generated by exposing various colon cancer cell lines to various concentrations of QHS.

FIG. 3b depicts the dose response curves generated by exposing various colon cancer cell lines to various concentrations of the β, β-QHS PEG dimer of the present invention.

FIG. 3c depicts the dose response curves generated by exposing various colon cancer cell lines to various concentrations of the α, β-QHS PEG dimer of the present invention.

Figure 3A:
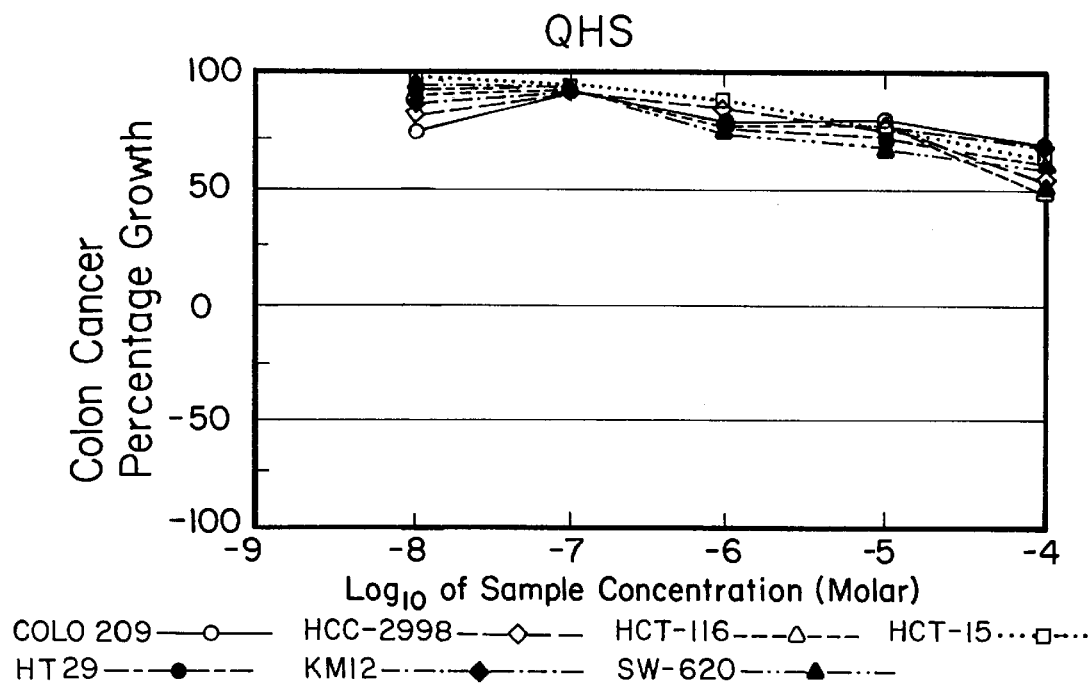
Figure 3B:
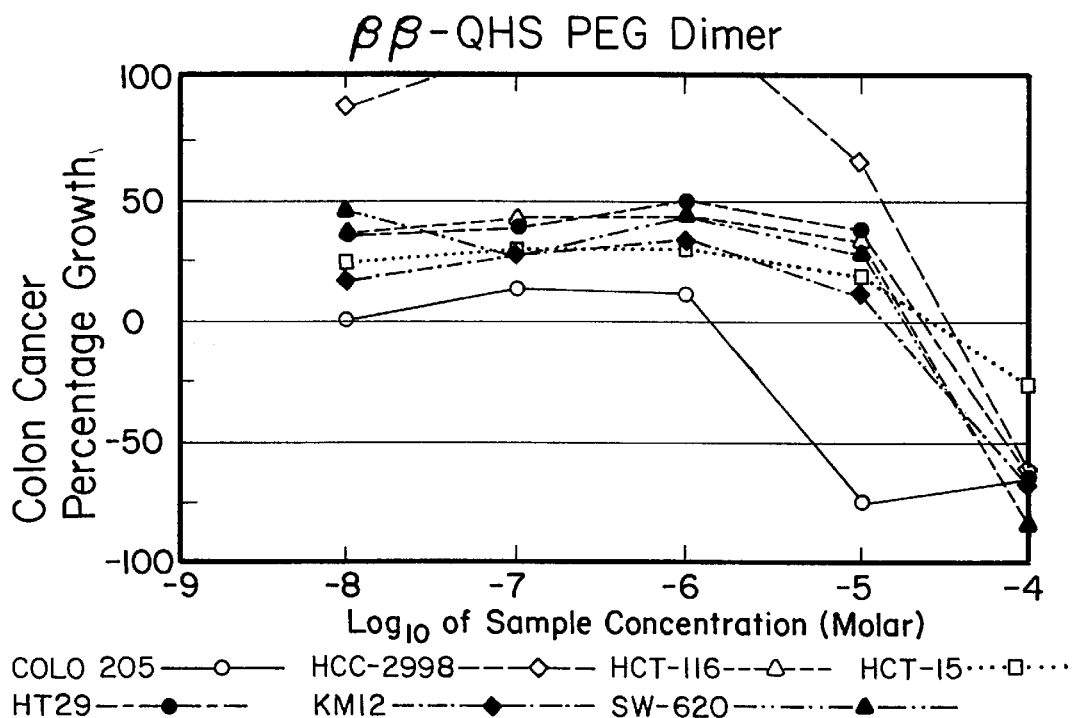
Figure 3C:
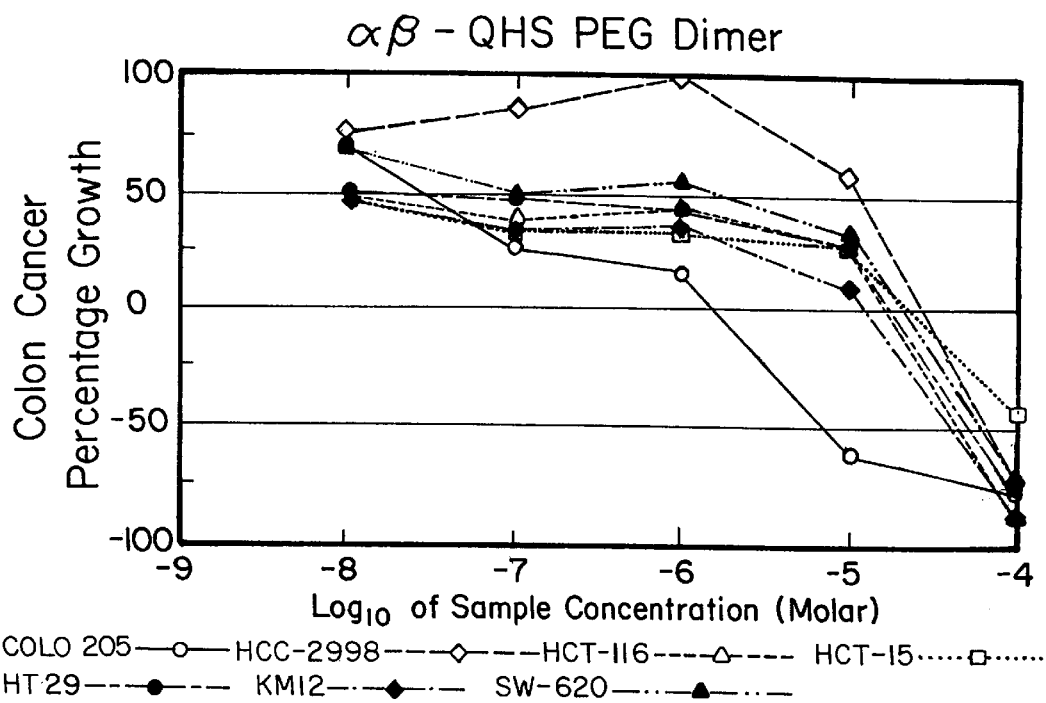
Figure 3D:
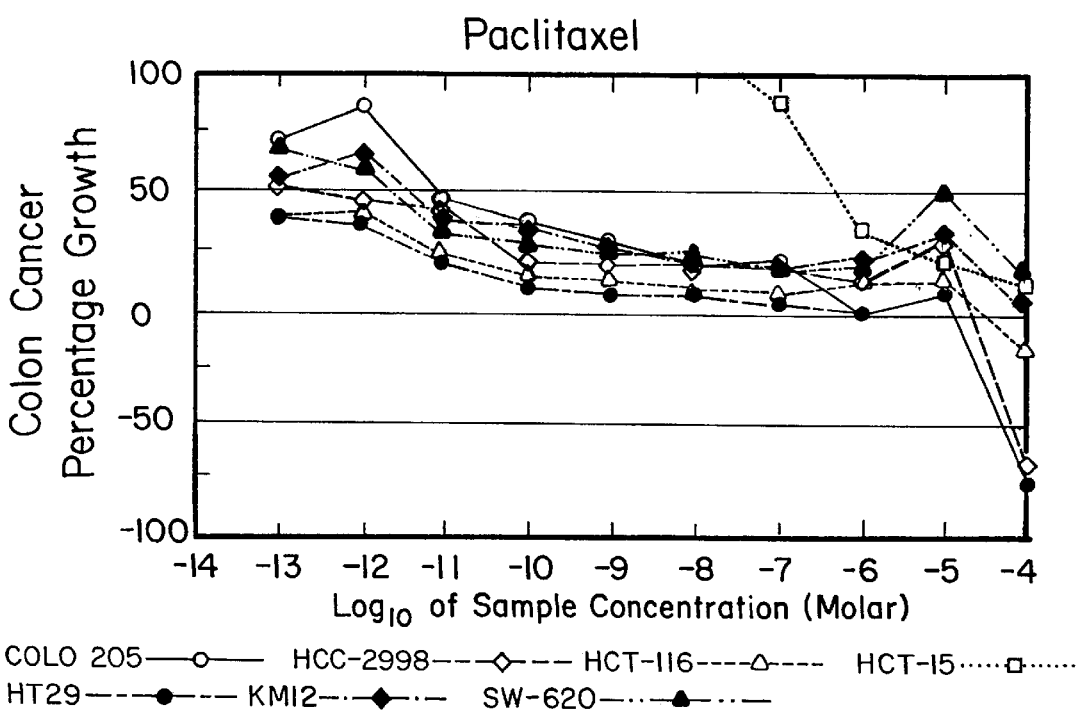

FIG. 3d depicts the dose response curves generated by exposing various colon cancer cell lines to various concentrations of paclitaxel.

Figure 4A:
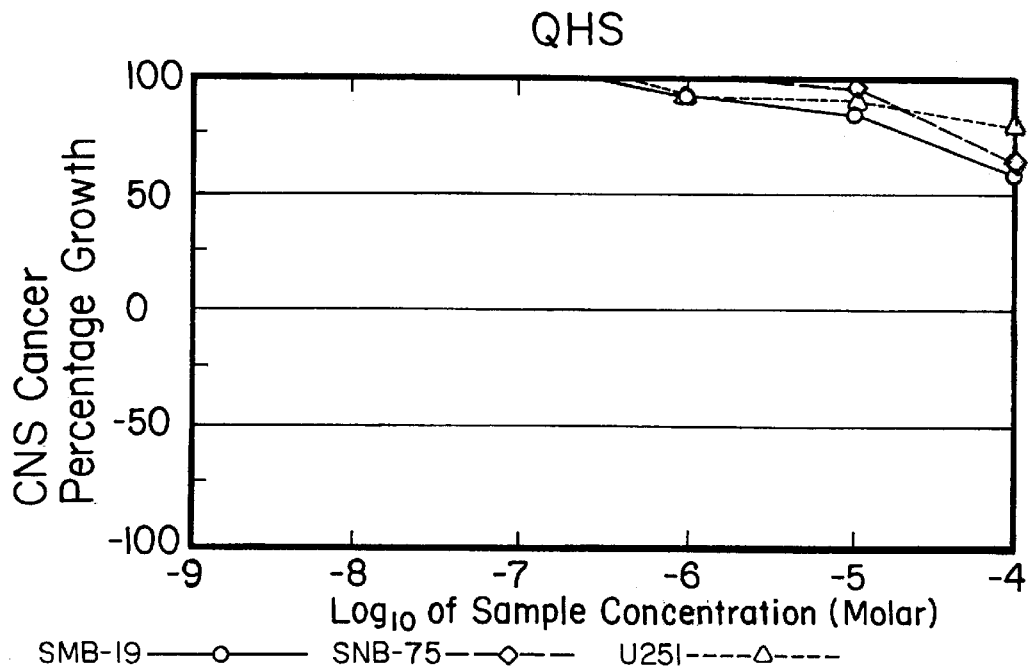

FIG. 4a depicts the dose response curves generated by exposing various CNS cancer cell lines to various concentrations of QHS.

Figure 4B:
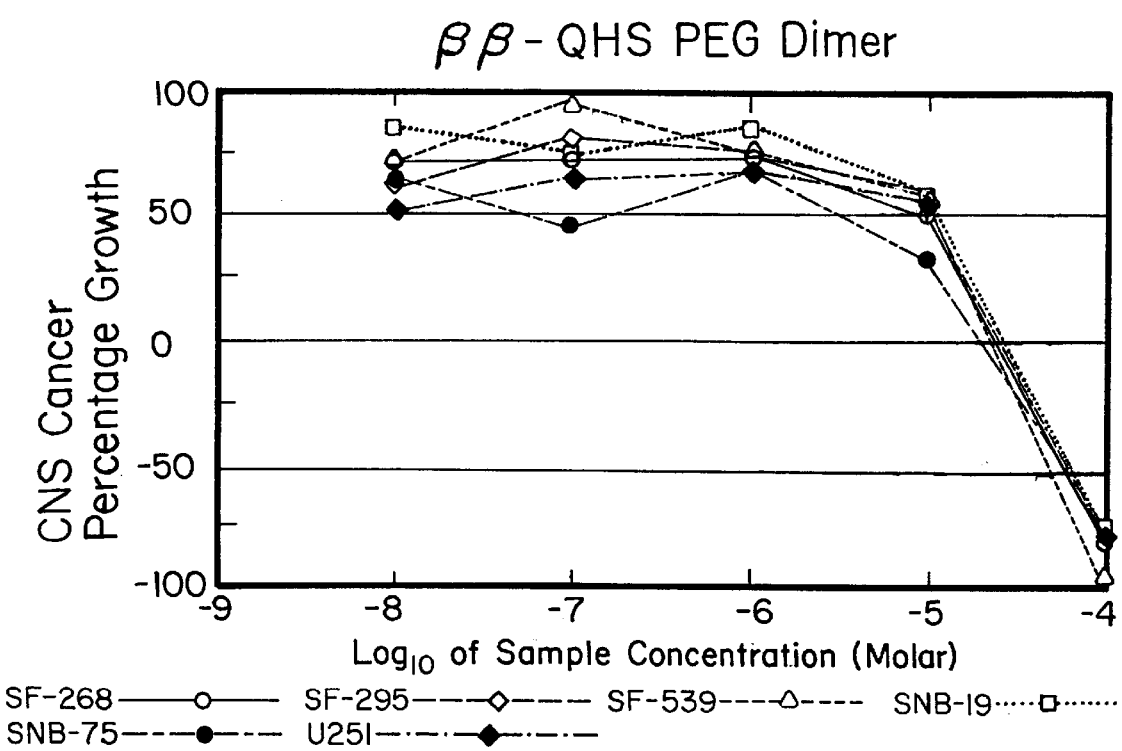

FIG. 4b depicts the dose response curves generated by exposing various CNS cancer cell lines to various concentrations of the β, β-QHS PEG dimer of the present invention.

Figure 4C:
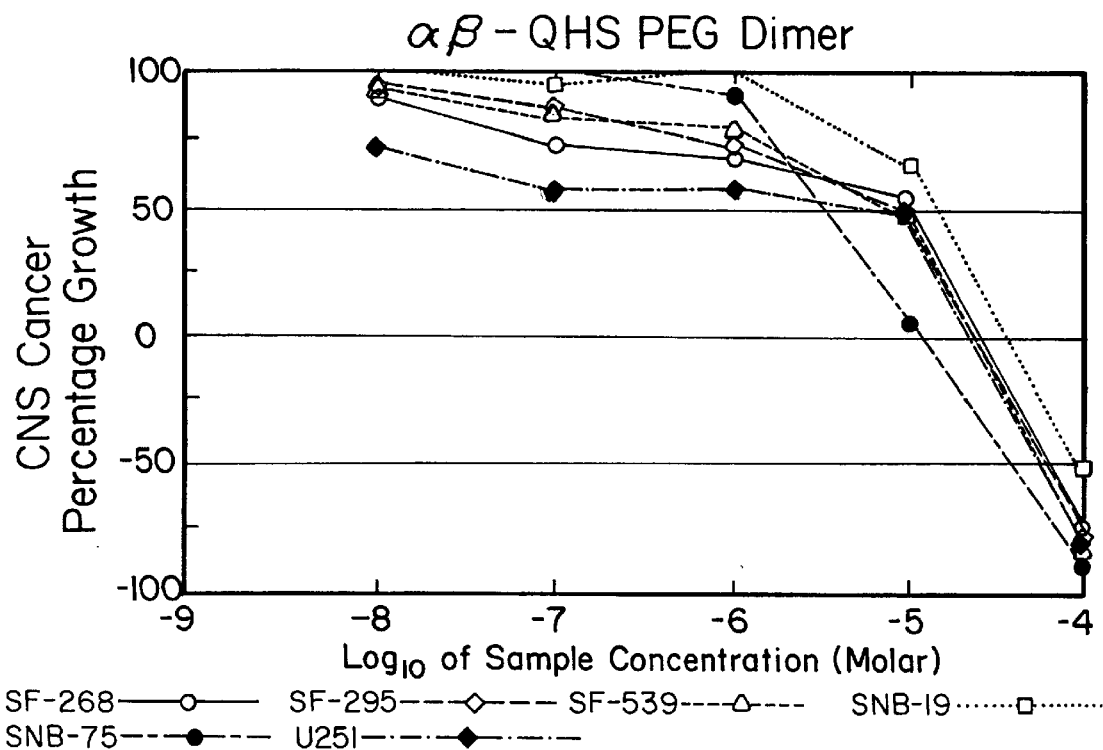

FIG. 4c depicts the dose response curves generated by exposing various CNS cancer cell lines to various concentrations of the α, β-QHS PEG dimer of the present invention.

Figure 4D:
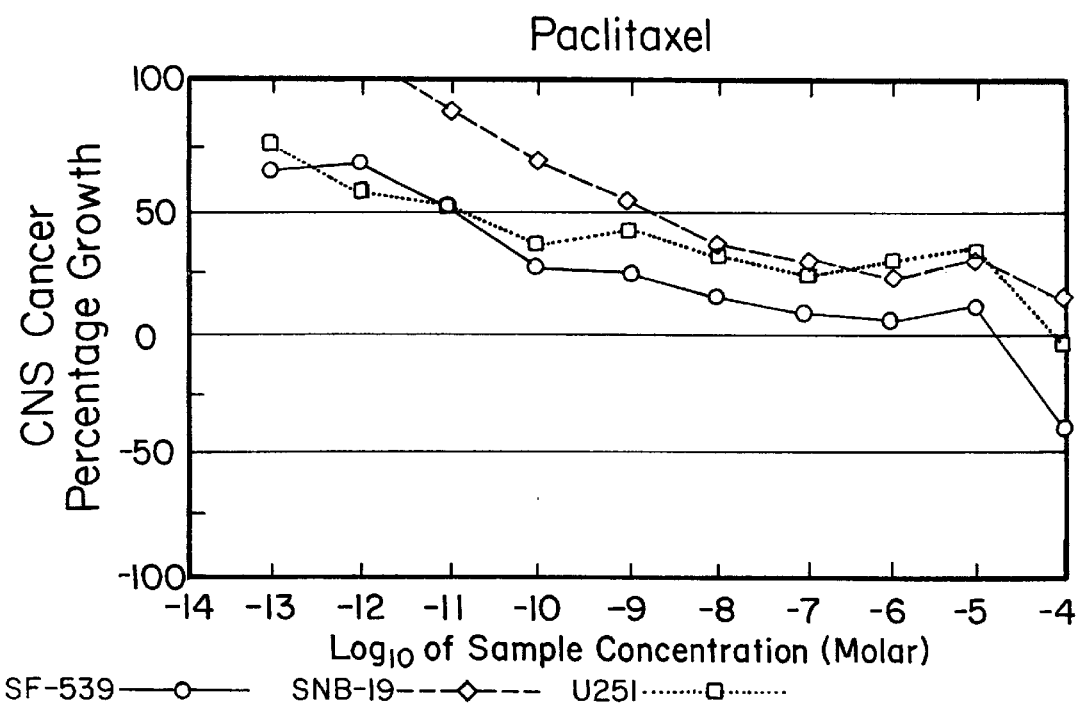

FIG. 4d depicts the dose response curves generated by exposing various CNS cancer cell lines to various concentrations of paclitaxel.

Figure 5A:
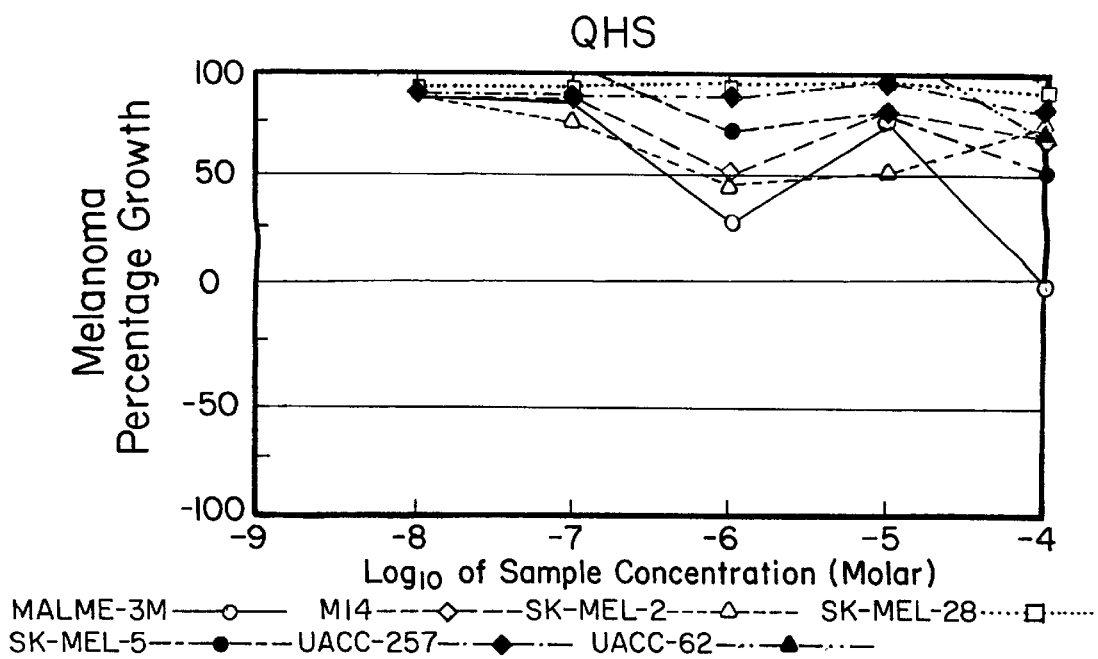

FIG. 5a depicts the dose response curves generated by exposing various melanoma cancer cell lines to various concentrations of QHS.

Figure 5B:
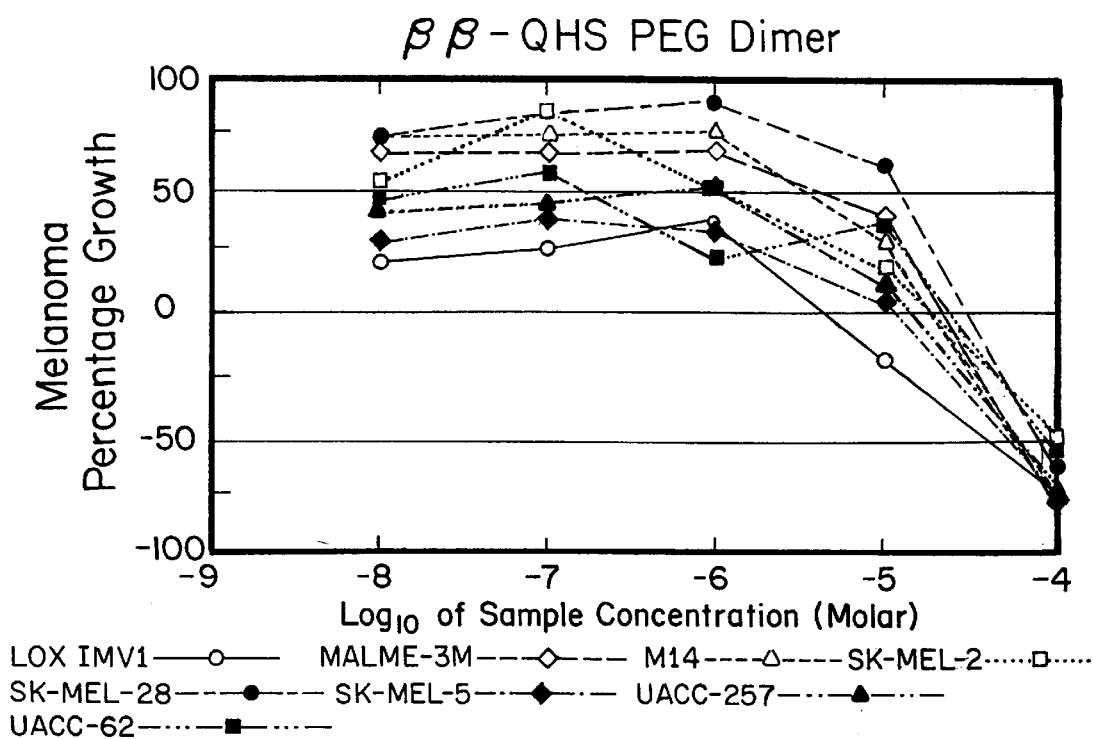

FIG. 5b depicts the dose response curves generated by exposing various melanoma cancer cell lines to various concentrations of the β, β-QHS PEG dimer of the present invention.

Figure 5C:
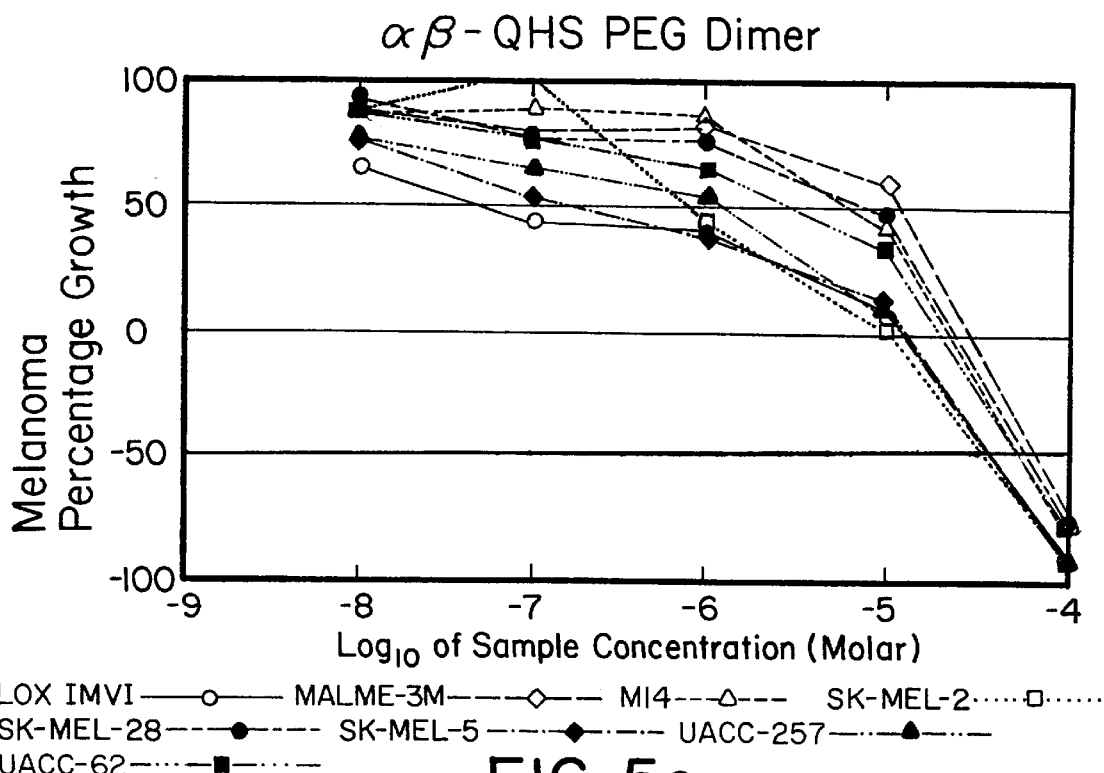

FIG. 5c depicts the dose response curves generated by exposing various melanoma cancer cell lines to various concentrations of the α, β-QHS PEG dimer of the present invention.

Figure 5D:
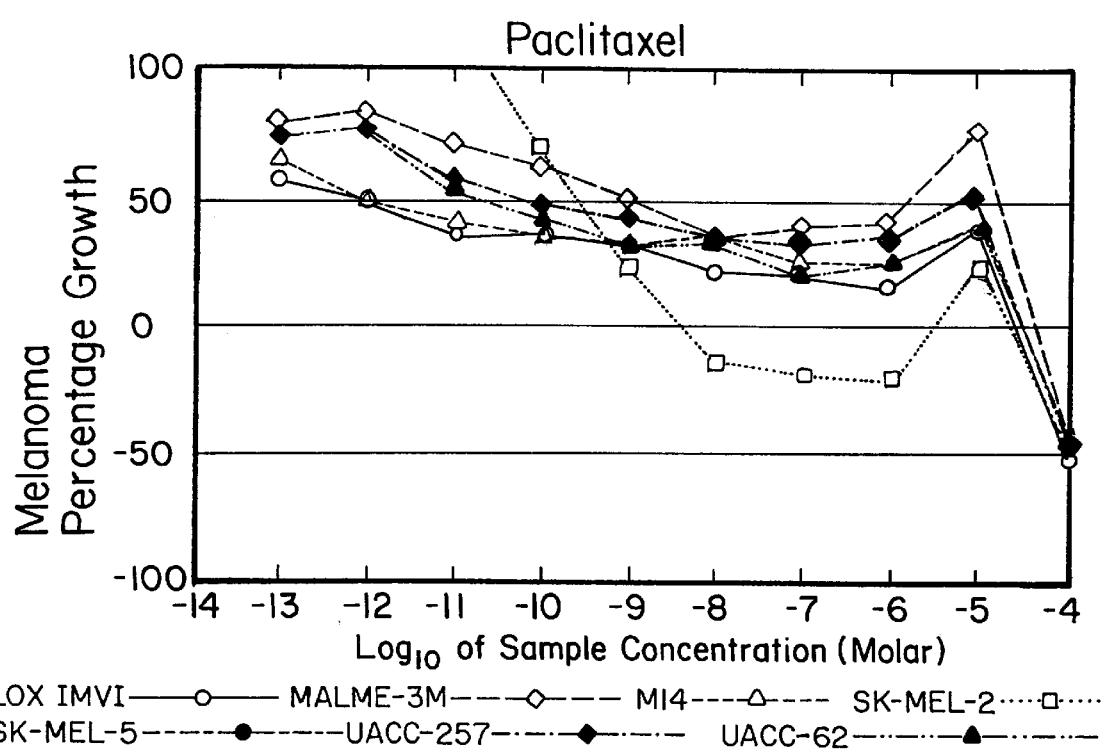

FIG. 5d depicts the dose response curves generated by exposing various melanoma cancer cell lines to various concentrations of paclitaxel.

Figure 6A:
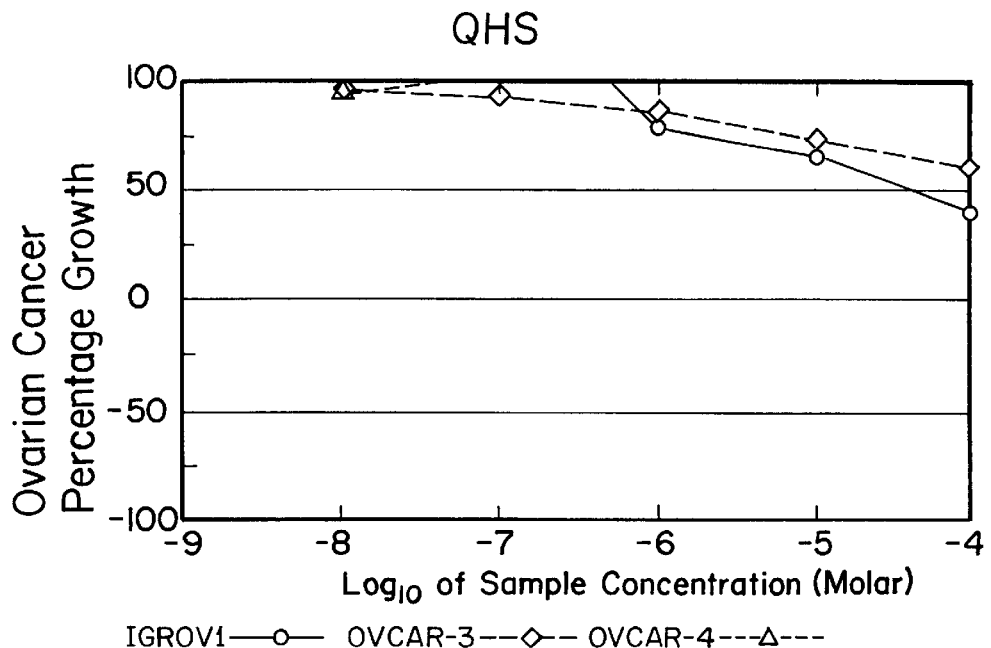

FIG. 6a depicts the dose response curves generated by exposing various ovarian cancer cell lines to various concentrations of QHS.

Figure 6B:
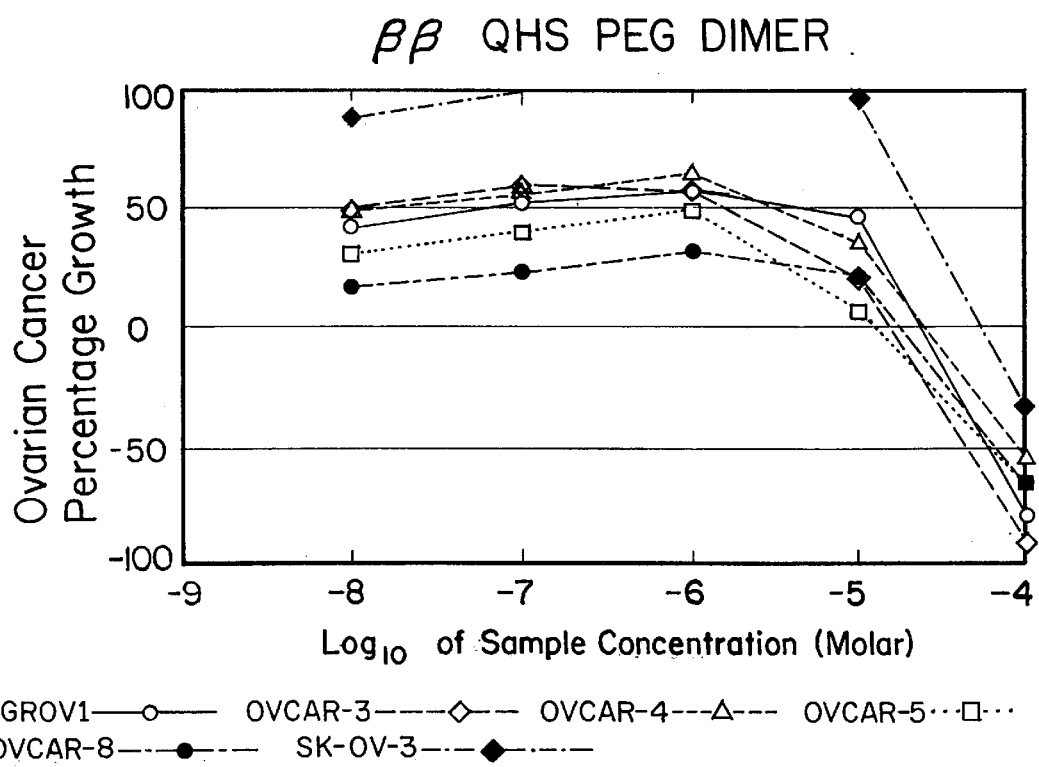

FIG. 6b depicts the dose response curves generated by exposing various ovarian cancer cell lines to various concentrations of the β, β-QHS PEG dimer of the present invention.

Figure 6C:
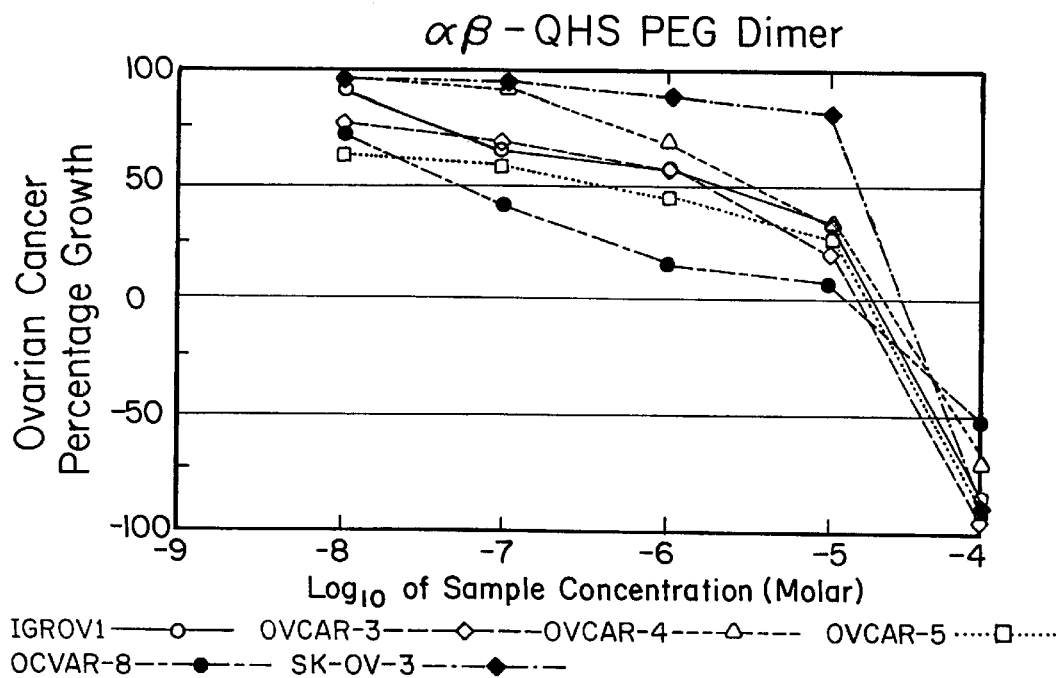

FIG. 6c depicts the dose response curves generated by exposing various ovarian cancer cell lines to various concentrations of the α, β-QHS PEG dimer of the present invention.

Figure 6D:
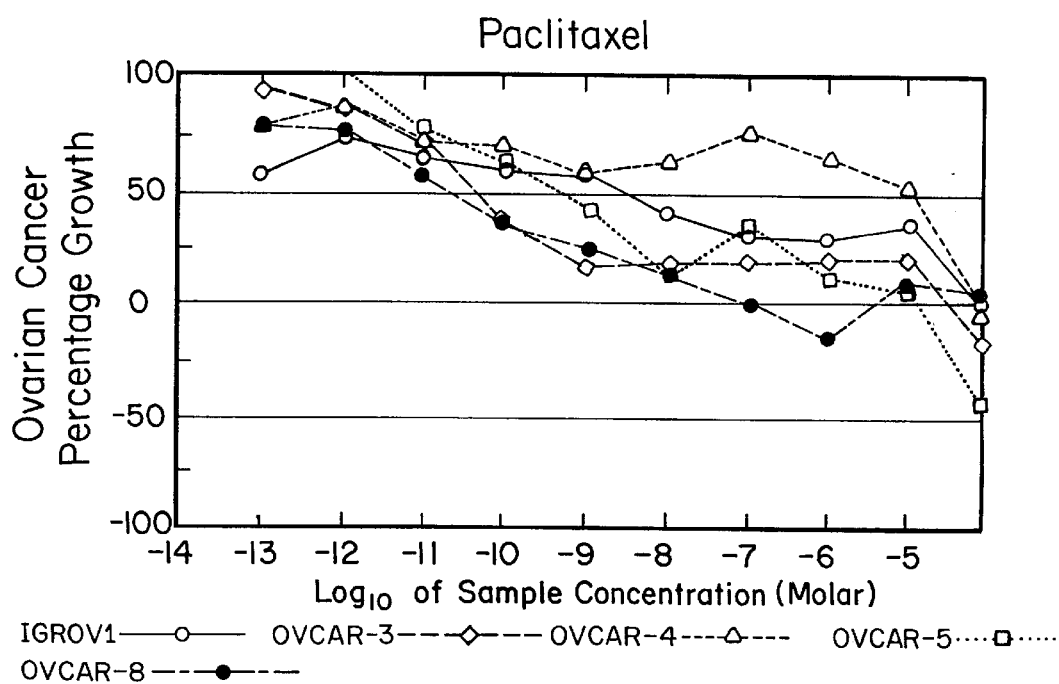

FIG. 6d depicts the dose response curves generated by exposing various ovarian cancer cell lines to various concentrations of paclitaxel.

Figure 7A:
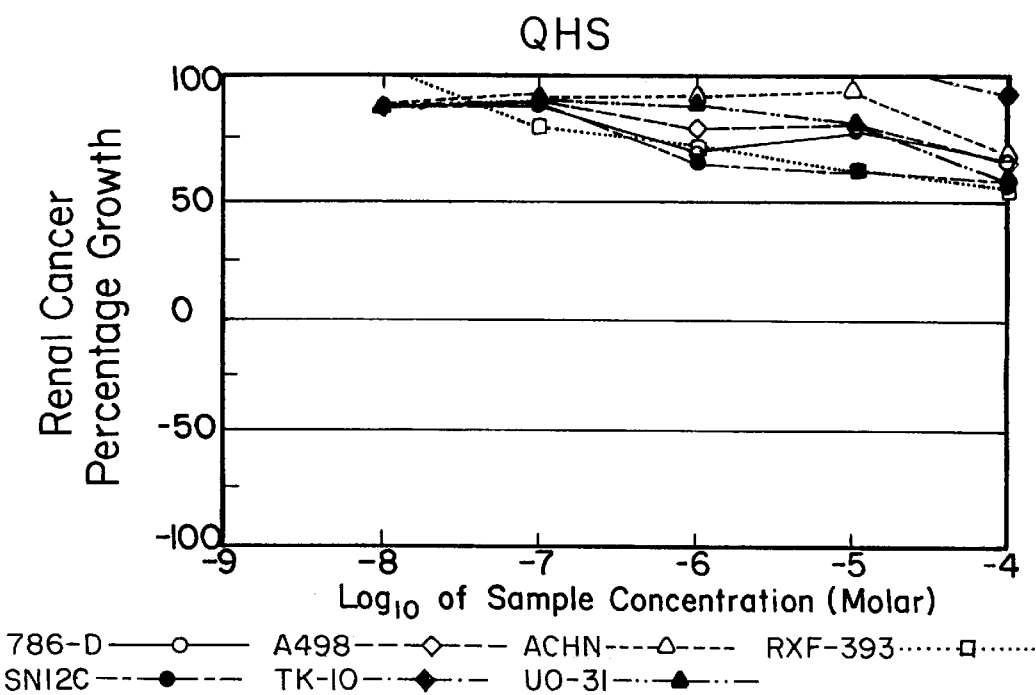

FIG. 7a depicts the dose response curves generated by exposing various renal cancer cell lines to various concentrations of QHS.

Figure 7B:
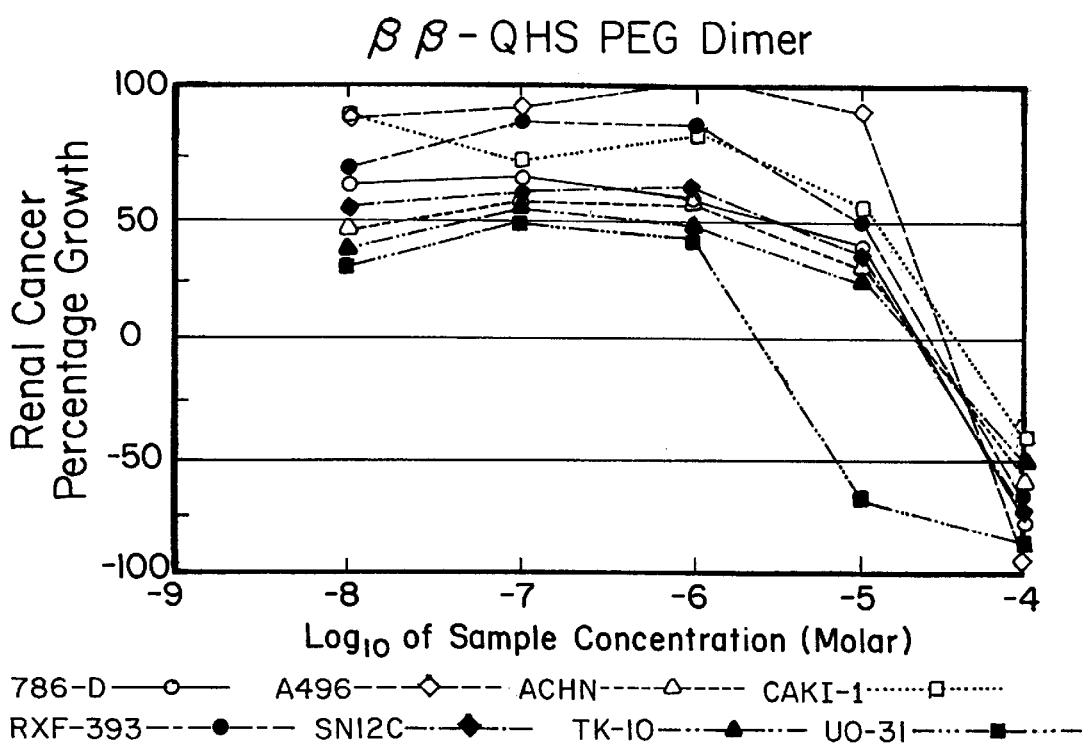

FIG. 7b depicts the dose response curves generated by exposing various renal cancer cell lines to various concentrations of the β, β-QHS PEG dimer of the present.

Figure 7C:
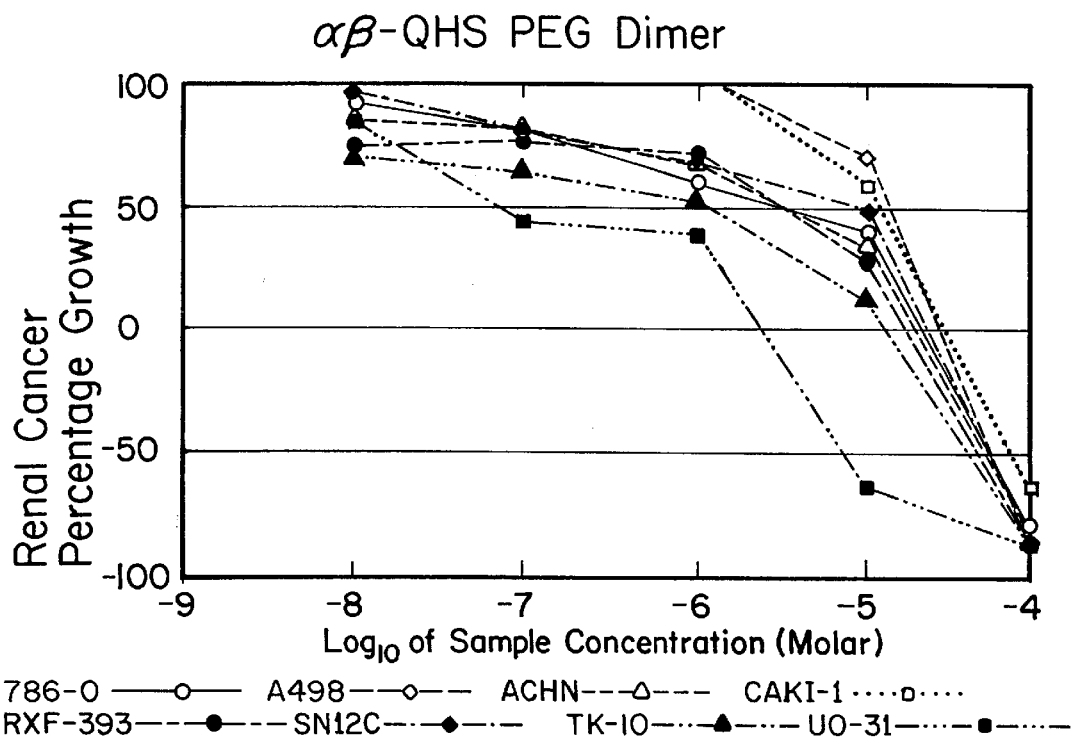

FIG. 7c depicts the dose response curves generated by exposing various renal cancer cell lines to various concentrations of the α, β-QHS PEG dimer of the present.

Figure 7D:
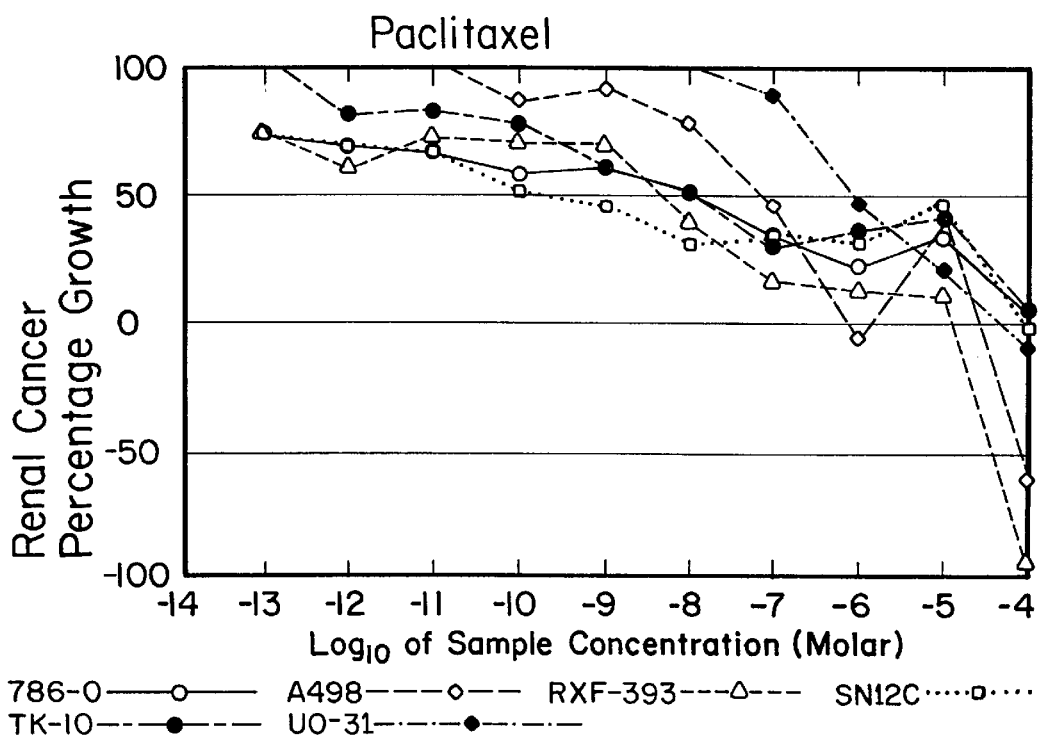

FIG. 7d depicts the dose response curves generated by exposing various renal cancer cell lines to various concentrations of paclitaxel.

Figure 8A:
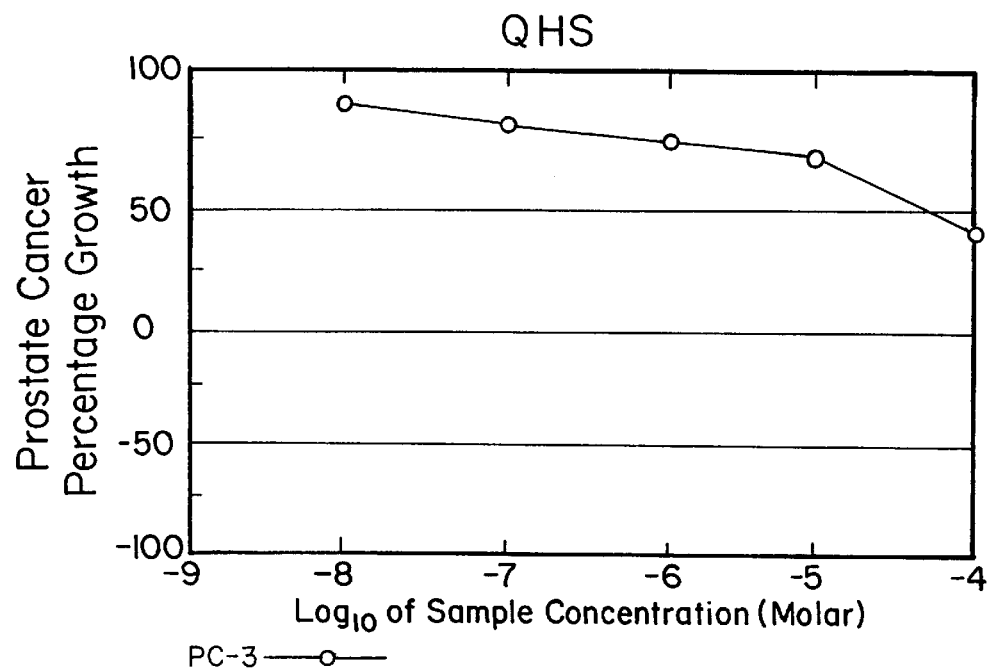

FIG. 8a depicts the dose response curves generated by exposing various prostate cancer cell lines to various concentrations of QHS.

Figure 8B:
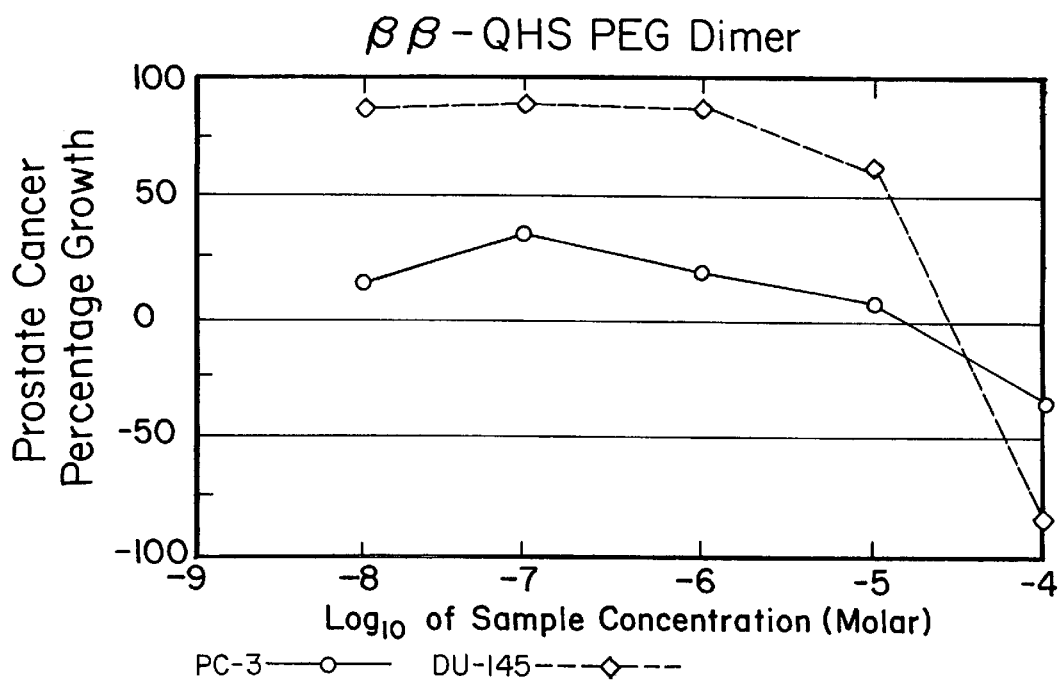

FIG. 8b depicts the dose response curves generated by exposing various prostate cancer cell lines to various concentrations of the β, β-QHS PEG dimer of the present.

Figure 8C:
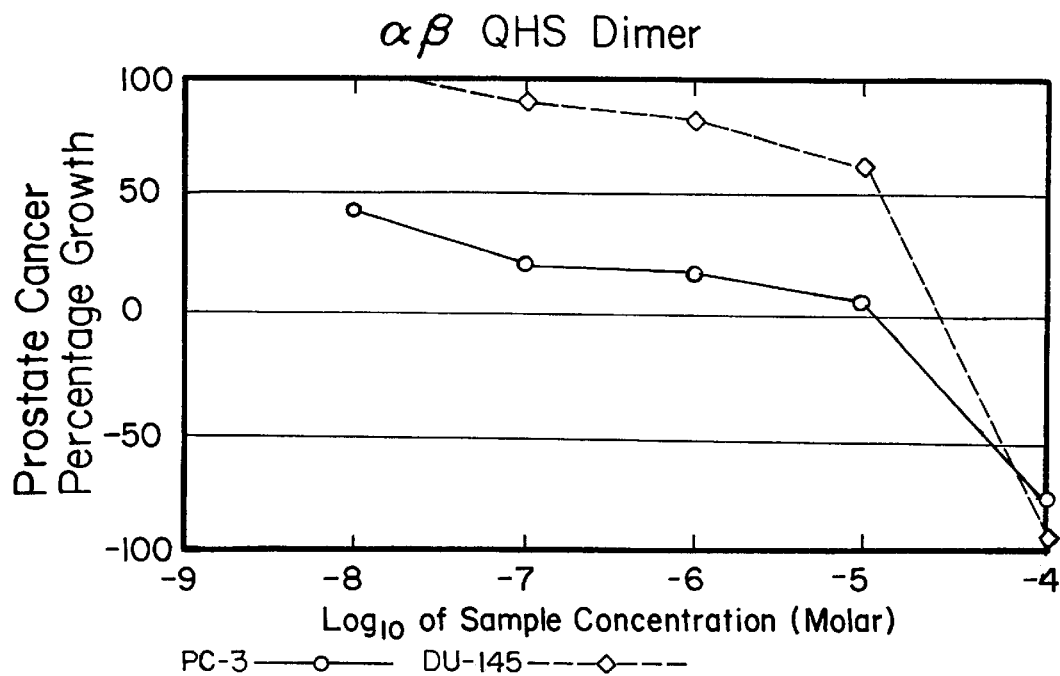

FIG. 8c depicts the dose response curves generated by exposing various prostate cancer cell lines to various concentrations of the α, β-QHS PEG dimer of the present.

Figure 8D:
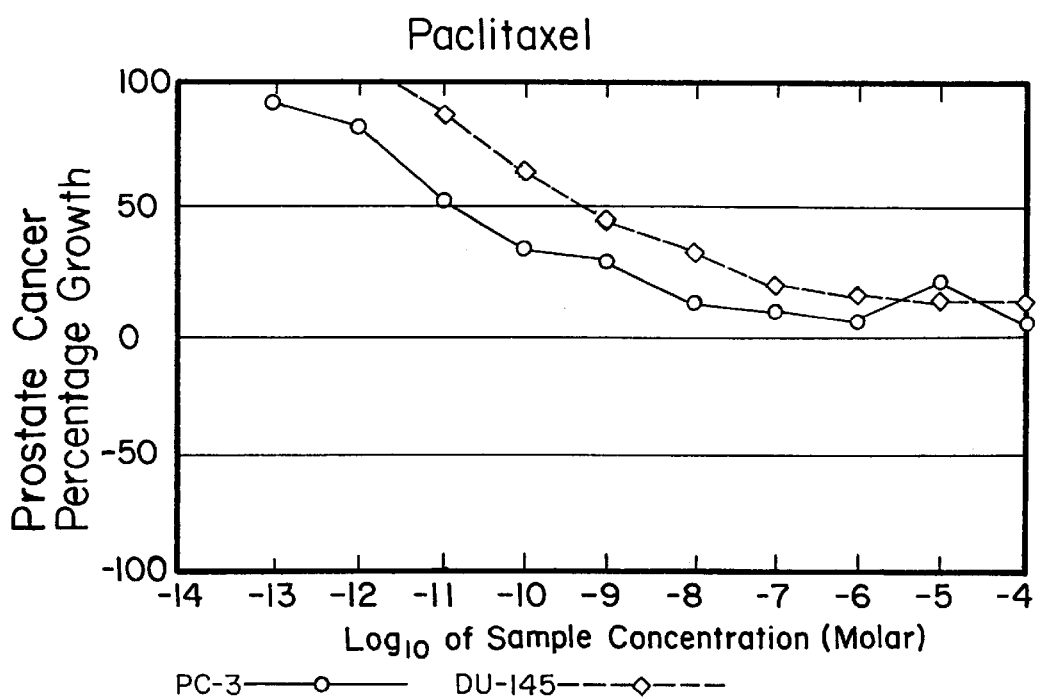

FIG. 8d depicts the dose response curves generated by exposing various prostate cancer cell lines to various concentrations of paclitaxel.

Figure 9A:
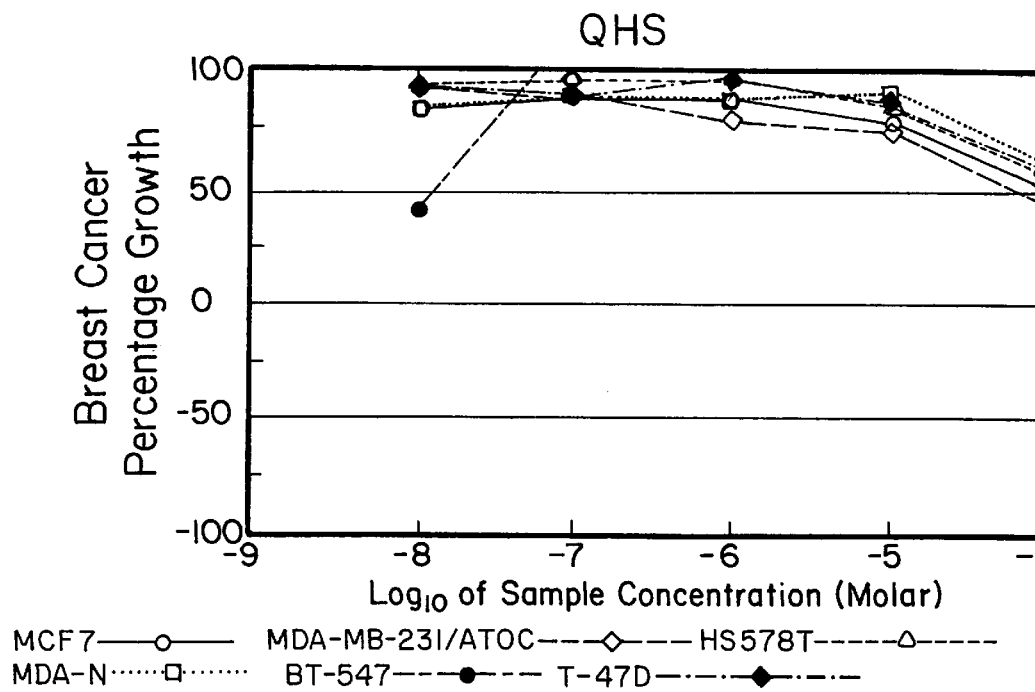

FIG. 9a depicts the dose response curves generated by exposing various breast cancer cell lines to various concentrations of QHS.

Figure 9B:
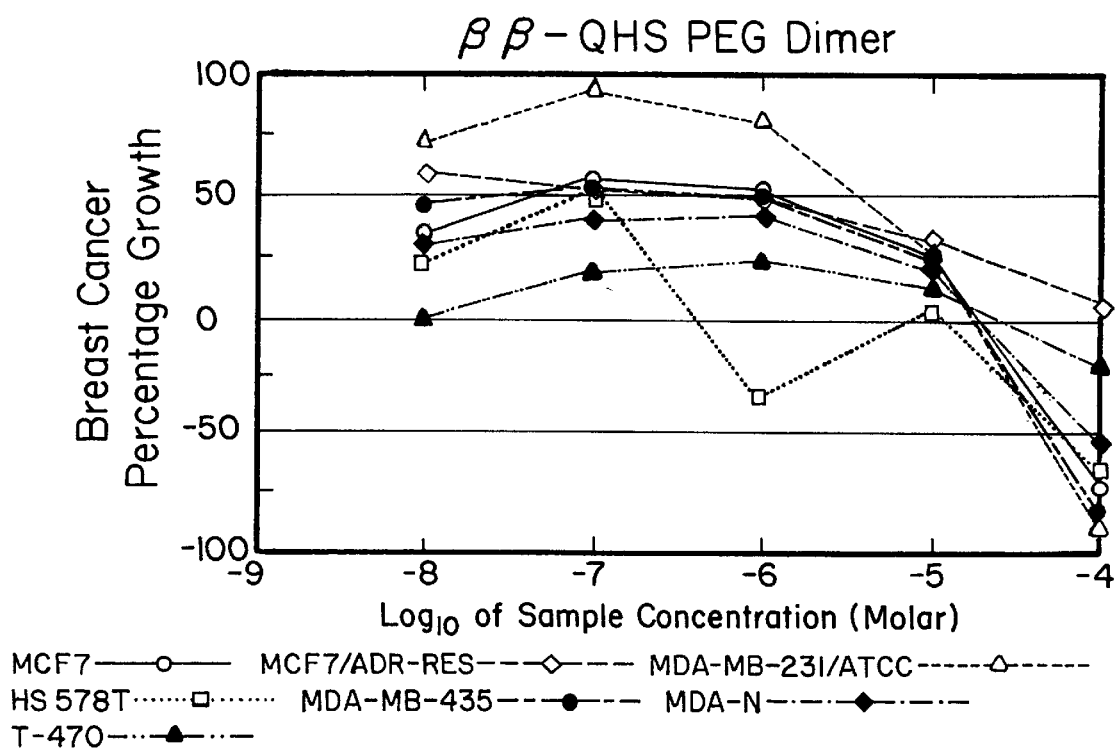

FIG. 9b depicts the dose response curves generated by exposing various breast cancer cell lines to various concentrations of the β, β-QHS PEG dimer of the present.

Figure 9C:
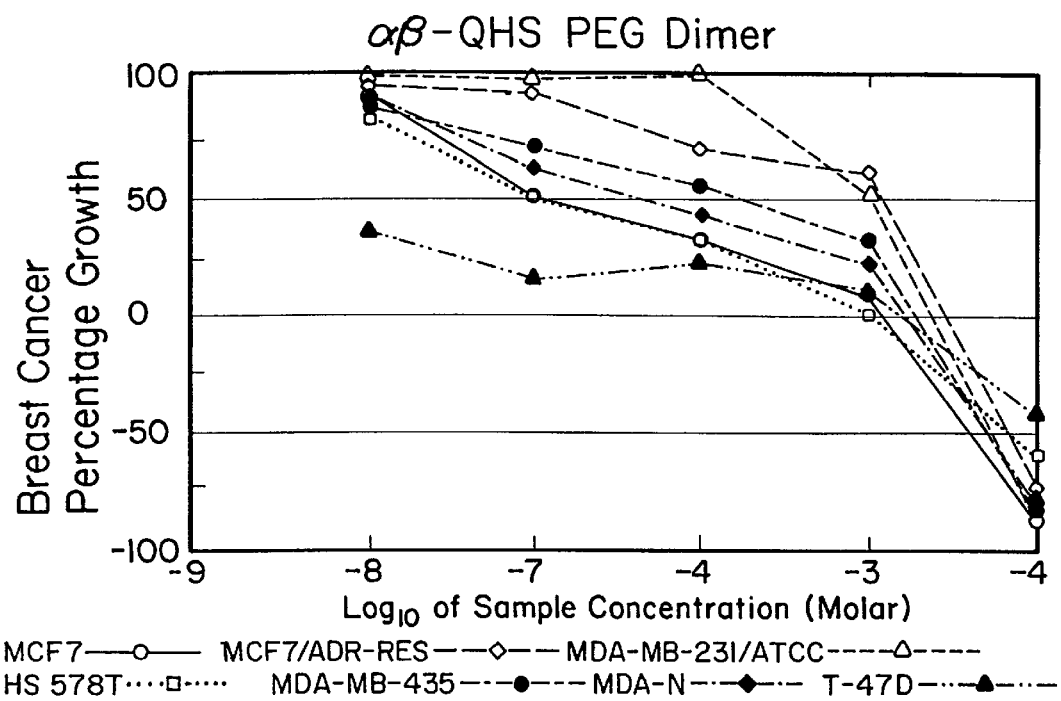

FIG. 9c depicts the dose response curves generated by exposing various breast cancer cell lines to various concentrations of the α, β-QHS PEG dimer of the present.

Figure 9D:
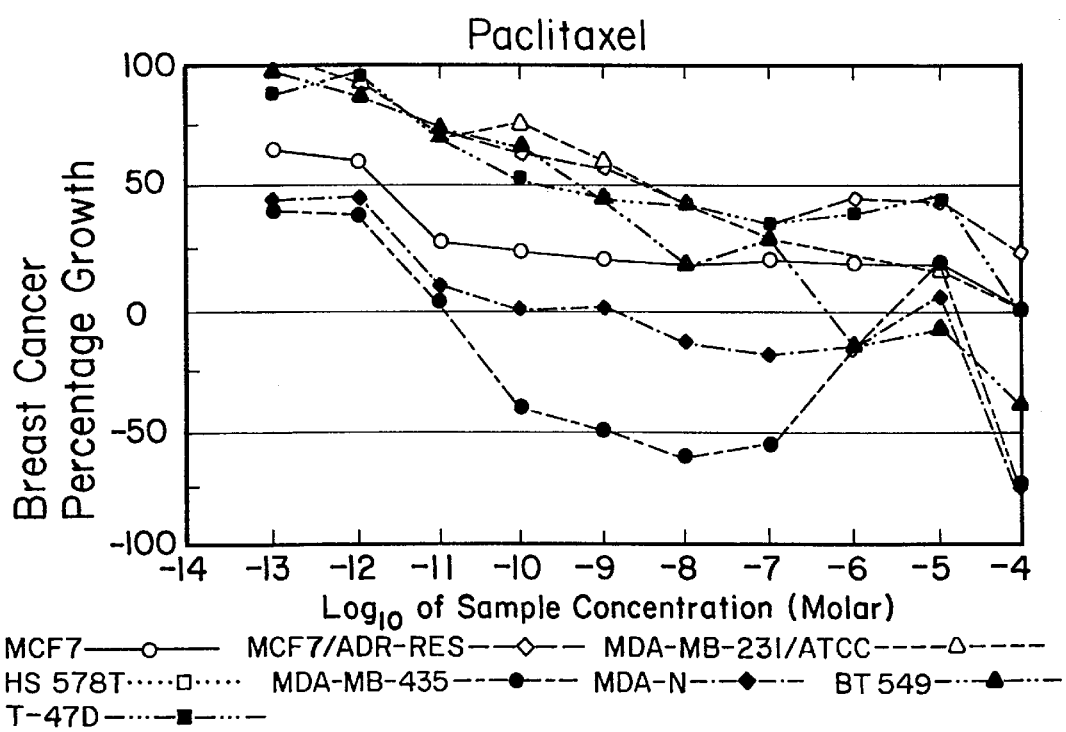

FIG. 9d depicts the dose response curves generated by exposing various breast cancer cell lines to various concentrations of paclitaxel.

DETAILED DESCRIPTION OF THE PREFERRED EMBODIMENT

The present invention provides a novel class of QHS-dimers of formula IV:

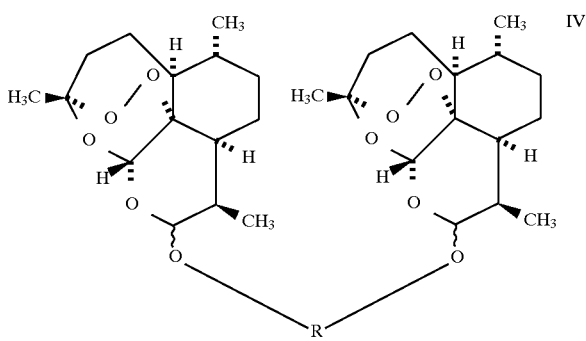

in which R is a linker such as a bivalent aromatic, arylene, lower alkylene, lower alkenylene, bivalent halide species, a bivalent protein, an atom, or —$CH_2CH_2$—$(XCH_2CH_2)$— where X is O, S, NY where Y is H (hydrogen) or alkenylene, and n is 0–20, or R is —X—Z—X— where X is a bivalent ester, carbamate, or carbonate species, and Z is a bivalent aromatic group, arylene, polyethylene glycol (PEG), lower alkylene, lower alkenylene, or a bivalent halide species. References to "lower alkylene," or "lower alkenylene," represents alkylenes, or alkenylenes of 1 to 20 carbon atoms, References to "halide" are compounds containing only carbon, hydrogen, and halogen, which fall into one of three general categories: Alkylene halides, arylene halide (in which a halogen is bonded to a carbon of an aromatic ring), and a vinylic halides (in which a halogen is bonded to a double-bonded carbon). Within these general categories of halides are specific halides, such as, allylic halides and benzylic halides. An atom or group that is attached to the carbon atom adjacent to one of the $sp^2$ carbon atoms is said to be in the allylic position or the benzylic position, respectively. The isomers of the invention include the α α, αβ, and β β conformations.

Examples of bivalent aromatic substituents include, but are not limited to, hydroxyphenylene, and bivalent bihydroxyphenyl. Typical alkanes include, but not limited to, methane, ethane, propane, and butane. Examples of halides include, but are not limited to, 2-chlorobutylene, 4-chloro-2-pentenylene, and 1-bromo-4-methyl-1-phenyl pentenylene.

The synthesis of a compound of structure IV can be accomplished by a wide variety of methods. The synthetic descriptions and specific examples that follow are only intended for the purposes of illustration, and are not to be construed as limiting in any manner to make compounds of the present invention by other methods.

In one embodiment a compound of structure IV, where R is —$(CH_2CH_2O)_n$—, and n is 1–20 (DHQHS-ether dimer), may be made by reacting DHQHS and polyethylene glycol, for example trimethylene glycol, or —$(CH_2CH_2O)_n$ where n is 3, with a Lewis acid such as $BF_3.Et_2O$ (Borontriflorate Etherate). A representative reaction scheme for the preparation of a DHQHS-PEG dimers and monomers is shown below.

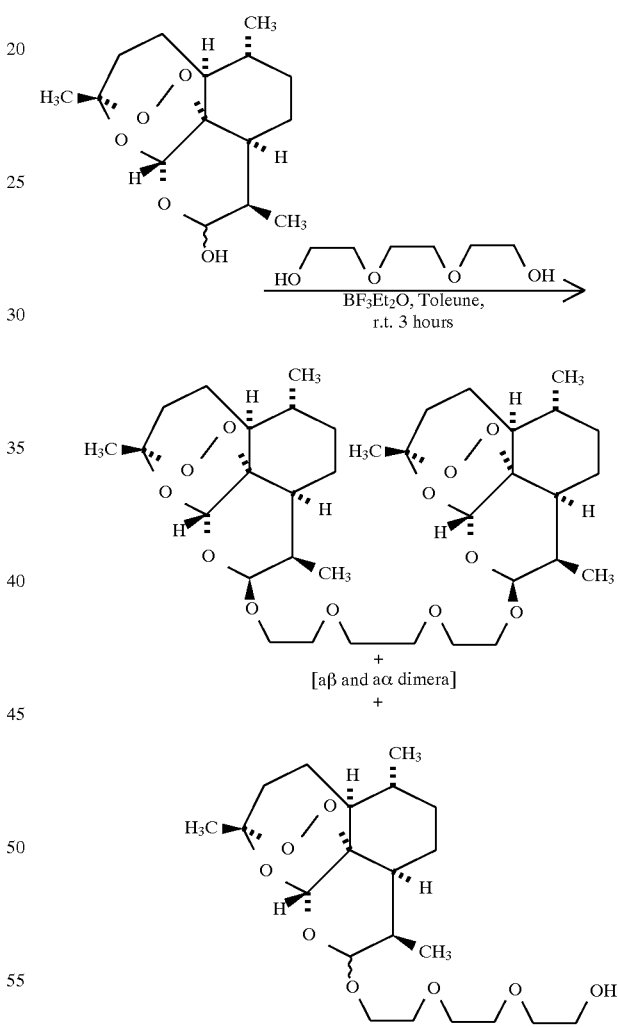

In a second embodiment a compound of structure IV, (DHQHS-carbamate dimer), where R is —X—Z—X—, where X is a bivalent carbamate and Z is a bivalent aromatic, arylene, bivalent halide species, lower alkylene, or lower alkenylene, is made by reacting DHQHS with di-isocyanate. A representative reaction scheme for the preparation of DHQHS-carbamate dimer is shown below.

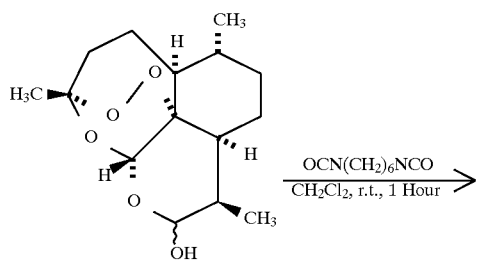

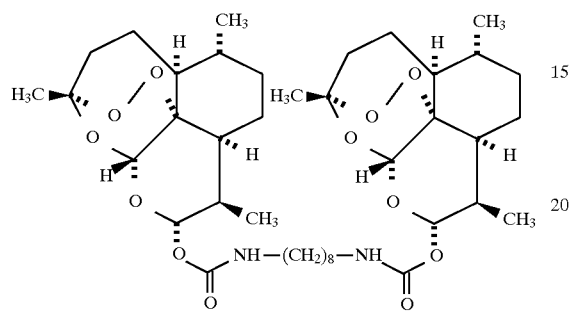

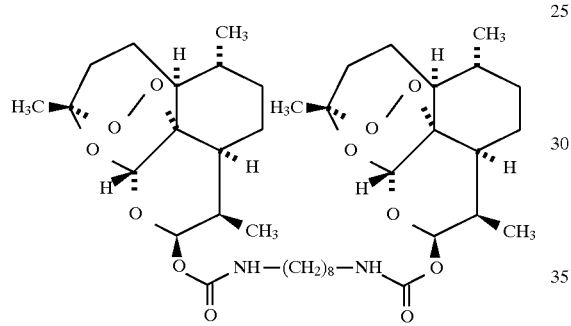

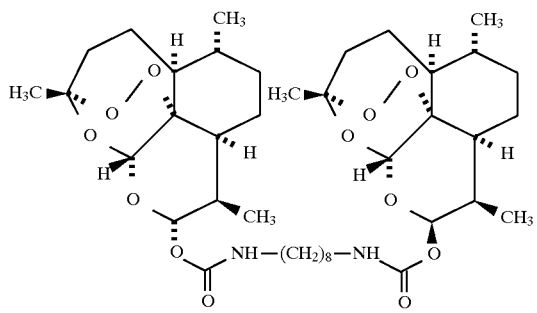

In a third embodiment a compound of structure IV, (DHQHS-ester dimer), where R is —X—Z—X— where X is a bivalent ester and Z is a bivalent aromatic group, arylene, a bivalent halide species, lower alkylene, or lower alkenylene, is made by reacting DHQHS with an acid chloride or a diacid, such as adopoyl chloride or adipic acid, respectively. A representative reaction scheme for the preparation of the α, α- DHQHS-ester dimer and its isomers is shown below.

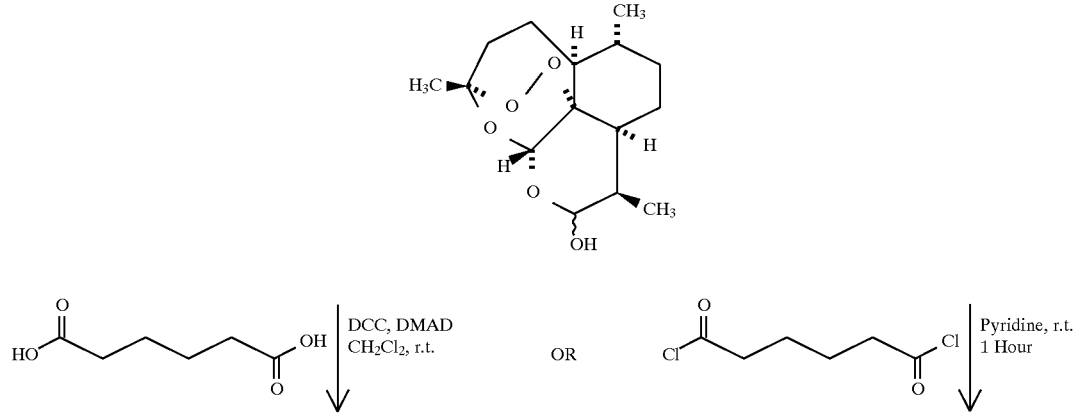

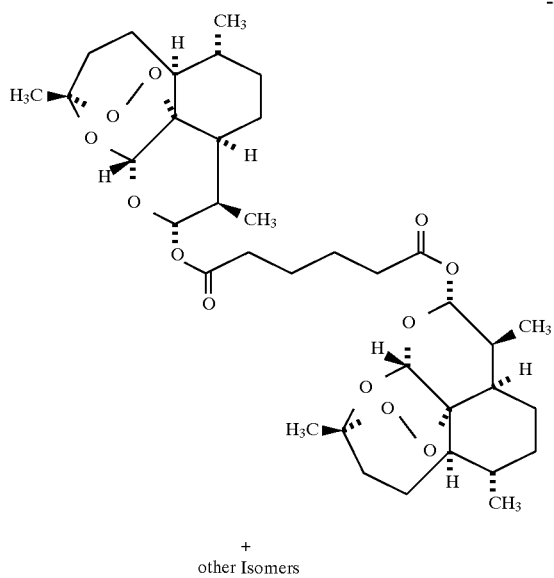

+
other Isomers

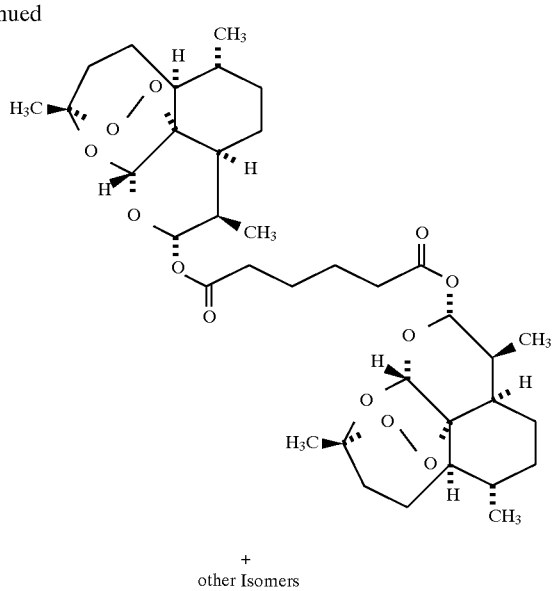

+
other Isomers

The other isomers are those isomers having the β, β- and α, β- conformations.

To determine the cytotoxicity of the DHQHS dimers of the present invention, screening assays were performed by the National Cancer Institute using a 60 cell line panel; some of these activities are summarized in Table I (set out below). The screening assay is performed on 96-well microtitre plates. Relatively high initial inoculation densities are used, in order to permit measurement of "time-zero" values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a nonroutine basis if appropriate solubility and/or prior biological information or other screening data so dictate. Duplicate wells are prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$M is: molecular weight of compound x $10^{-4} \times 0.04$. After a 48 hour incubation (37° C.) with the test compound, the cells are fixed in situ to the bottoms of the microtitre wells by addition of 50 μl of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. At this value the increase from time $t_{zero}$ in the number or mass of cells in the test well is only 50% as much as the corresponding increase in the control well during this period of the experiment. A drug effect of this intensity is interpreted as primary growth inhibition.

TGI is the concentration for which PG=0. At this value the number or mass of cells in the well at the end of the experiment equals the number or mass of cells in the well at time $t_{zero}$ drug effect of this intensity is regarded as cytostasis.

$LC_{50}$ is the concentration for which the PG=−50. At this value, the number or mass of cells in the test well at the end of the experiment is half that at time $t_{zero}$. This is interpreted as cytotoxicity.

TABLE I

| Panel/ | $\text{Log}_{10}$ $\text{GI}_{50}$ | | | | $\text{Log}_{10}$ TGI | | | | $\text{Log}_{10}$ $\text{LC}_{50}$ | | | |
| --- | --- | --- | --- | --- | --- | --- | --- | --- | --- | --- | --- | --- |
| | | HDQHS Dimer | | Pacli- | | HDQHS Dimer | | Pacli- | | HDQHS Dimer | | Pacli- |
| Cell line | QHS | β, β | α, β | taxel | QHS | β, β | α, β | taxel | QHS | β, β | α, β | taxel |
| Leukemia | | | | | | | | | | | | |
| CCRF-CEM | — | — | −7.23 | −11.61 | — | −4.66 | −5.14 | >−4.00 | — | −4.04 | −4.30 | >−4.00 |
| HL-60(TB) | −4.26 | <−8.00 | <−8.00 | −11.57 | >−4.00 | <−8.00 | <−8.00 | −4.53 | >−4.00 | — | −7.56 | >−4.00 |
| K-562 | −4.33 | <−8.00 | −7.74 | −10.83 | >−4.00 | −5.34 | −5.82 | >−4.00 | >−4.00 | −4.15 | −4.48 | >−4.00 |
| MOLT-4 | −4.73 | <−8.00 | <−8.00 | −11.07 | >−4.00 | −5.80 | −5.93 | >−4.00 | >−4.00 | −4.55 | −4.73 | >−4.00 |
| RPMI-8226 | >−4.00 | <−8.00 | <−8.00 | <−13.00 | >−4.00 | −5.50 | −5.76 | >−4.00 | >−4.00 | >−4.00 | −4.28 | >−4.00 |
| SR | >−4.00 | <−8.00 | <−8.00 | −8.34 | >−4.00 | <−8.00 | <−8.00 | >−4.00 | >−4.00 | >−4.00 | −4.22 | >−4.00 |
| Non-Small Cell Lung Cancer | | | | | | | | | | | | |
| A549/ATCC | −4.17 | −5.33 | −5.57 | — | >−4.00 | −4.68 | −4.69 | — | >−4.00 | −4.27 | −4.25 | — |
| EKVX | >−4.00 | <−8.00 | −5.91 | — | >−4.00 | −4.69 | −4.66 | — | >−4.00 | −4.08 | −4.17 | — |
| HOP-62 | >−4.00 | −5.27 | −4.92 | −9.67 | >−4.00 | −4.68 | −4.59 | −4.80 | >−4.00 | −4.33 | −4.25 | −4.10 |
| HOP-92 | >−4.00 | −5.44 | −5.50 | — | >−4.00 | −4.73 | −4.75 | — | >−4.00 | −4.35 | −4.35 | — |
| NCI-H226 | >−4.00 | −7.59 | −4.79 | — | >−4.00 | −5.01 | −4.47 | — | >−4.00 | −4.31 | −4.16 | — |
| NCI-H23 | >−4.00 | — | −5.80 | — | >−4.00 | −4.80 | −4.79 | — | >−4.00 | −4.21 | −4.29 | — |
| NCI-H322M | — | −4.75 | −4.87 | −10.12 | — | −4.48 | −4.57 | −4.46 | — | −4.22 | −4.26 | >−4.00 |
| NCI-H460 | >−4.00 | −5.37 | −5.03 | −12.16 | >−4.00 | −4.59 | −4.53 | −4.92 | >−4.00 | −4.11 | −4.06 | >−4.00 |
| NCI-H522 | — | — | −6.13 | <−13.00 | — | −4.70 | −4.78 | −11.20 | — | −4.19 | −4.29 | >−4.00 |
| Colon Cancer | | | | | | | | | | | | |
| COLO 205 | >−4.00 | <−8.00 | −7.57 | −11.07 | >−4.00 | −5.90 | −5.84 | — | >−4.00 | −5.33 | −5.20 | >−4.41 |
| HCC-2998 | >−4.00 | −4.91 | −4.99 | −12.34 | >−4.00 | −4.53 | −4.61 | −4.77 | >−4.00 | −4.15 | −4.23 | −4.26 |
| HCT-116 | −4.18 | <−8.00 | <−8.0 | <−13.00 | >−4.00 | −4.77 | −4.81 | −4.82 | >−4.00 | −4.36 | −4.39 | >−4.00 |
| HCT-15 | >−4.00 | <−8.00 | <−8.0 | −6.37 | >−4.00 | −4.70 | −4.71 | >−4.00 | >−4.00 | >−4.00 | −4.02 | >−4.00 |
| HT29 | >−4.00 | <−8.00 | −7.85 | <−13.00 | >−4.00 | −4.67 | −4.77 | — | >−4.00 | −4.20 | −4.26 | −4.39 |
| KM12 | >−4.00 | <−8.00 | <−8.0 | −11.43 | >−4.00 | −4.90 | −4.95 | −4.36 | >−4.00 | −4.30 | −4.46 | >−4.00 |
| SW-620 | >−4.00 | <−8.00 | — | −11.60 | >−4.00 | −4.80 | −4.76 | >−4.00 | >−4.00 | −4.37 | −4.30 | >−4.00 |
| CNS Cancer | | | | | | | | | | | | |
| SF-268 | — | −5.00 | −5.00 | — | — | −4.60 | −4.63 | — | — | −4.20 | −4.25 | — |
| SF-295 | — | −5.09 | −5.20 | — | — | −4.62 | −4.68 | — | — | −4.23 | −4.32 | — |
| SF-539 | — | −4.99 | −5.22 | −11.09 | — | −4.65 | −4.69 | — | — | −4.32 | −4.33 | >−4.00 |
| SNB-19 | >−4.00 | −4.94 | −4.90 | −8.98 | >−4.00 | −4.56 | −4.49 | >−4.00 | >−4.00 | −4.18 | −4.07 | >−4.00 |
| SNB-75 | >−4.00 | — | −5.54 | — | >−4.00 | −4.72 | −4.98 | — | >−4.00 | −4.26 | −4.47 | — |
| U251 | >−4.00 | −5.00 | −5.67 | −11.29 | >−4.00 | −4.63 | −4.69 | −4.32 | >−4.00 | −4.26 | −4.32 | −4.15 |
| Melanoma | | | | | | | | | | | | |
| LOX-IMVI | — | <−8.00 | −7.26 | −11.80 | — | −5.00 | −4.89 | −4.65 | — | −4.39 | −4.41 | >−4.15 |
| MALME-3M | — | −5.47 | −4.96 | — | −4.06 | −4.70 | −4.60 | −4.46 | >−4.00 | −4.28 | −4.25 | −4.11 |
| M14 | — | −5.50 | −5.26 | −11.73 | >−4.00 | −4.76 | −4.69 | −4.62 | >−4.00 | −4.28 | −4.29 | −4.13 |
| SK-MEL-2 | — | −6.02 | −6.13 | −9.53 | >−4.00 | −4.81 | −5.08 | — | >−4.00 | −4.10 | −4.43 | >−4.00 |
| SK-MEL-28 | >−4.00 | −4.94 | −5.21 | — | >−4.00 | −4.56 | −4.66 | — | >−4.00 | −4.17 | −4.28 | — |
| SK-MEL-5 | −4.10 | <−8.00 | −6.80 | — | >−4.00 | −4.98 | −4.92 | — | >−4.00 | −4.39 | −4.44 | — |
| UACC-257 | >−4.00 | <−8.00 | −5.99 | −10.30 | >−4.00 | −4.92 | −4.94 | −4.52 | >−4.00 | −4.31 | −4.45 | −4.03 |
| UACC-62 | >−4.00 | −6.75 | −5.61 | −10.46 | >−4.00 | −4.64 | −4.72 | −4.71 | >−4.00 | −4.12 | −4.25 | −4.19 |
| Ovarian Cancer | | | | | | | | | | | | |
| IGROV1 | −4.31 | — | −5.69 | −8.61 | >−4.00 | −4.64 | −4.73 | −4.19 | >−4.00 | −4.24 | −4.33 | >−4.00 |
| OVCAR-3 | — | −5.82 | −5.79 | −10.40 | — | −4.82 | −4.82 | −4.55 | — | −4.37 | −4.39 | >−4.00 |
| OVCAR-4 | — | −5.52 | −5.47 | −5.00 | — | −4.61 | −4.69 | −4.19 | — | −4.05 | −4.20 | >−4.00 |
| OVCAR-5 | >−4.00 | <−8.00 | −6.29 | −9.38 | >−4.00 | −4.92 | −4.77 | −4.92 | >−4.00 | −4.23 | −4.35 | >−4.00 |
| OVCAR-8 | >−4.00 | <−8.00 | −7.24 | −10.75 | >−4.00 | −4.77 | −4.90 | — | >−4.00 | −4.21 | −4.26 | >−4.00 |
| SKOV3 | — | −4.65 | −4.82 | — | — | −4.27 | −4.52 | — | — | >−4.00 | −4.23 | — |
| Renal Cancer | | | | | | | | | | | | |
| 786-0 | >−4.00 | −5.97 | −5.67 | −8.01 | >−4.00 | −4.74 | −4.72 | >−4.00 | >−4.00 | −4.33 | −4.33 | >−4.00 |
| A498 | >−4.00 | −4.97 | −4.90 | −7.14 | >−4.00 | −4.52 | −4.60 | — | >−4.00 | −4.26 | −4.29 | −4.13 |
| ACHN | >−4.00 | — | −5.57 | — | >−4.00 | −4.73 | −4.76 | −4.90 | >−4.00 | −4.18 | −4.36 | −4.45 |
| CAKI-1 | — | −5.05 | −4.97 | — | — | −4.50 | −4.56 | −4.04 | — | >−4.00 | −4.15 | >−4.00 |
| RXF-393 | −4.08 | −5.16 | −5.58 | −8.32 | >−4.00 | −4.67 | −4.75 | >−4.00 | >−4.00 | −4.30 | −4.31 | >−4.00 |
| SN12C | −4.21 | −5.84 | −5.26 | −9.53 | >−4.00 | −4.74 | −4.66 | −4.29 | >−4.00 | −4.31 | −4.28 | >−4.00 |
| TK-10 | >−4.00 | — | −6.03 | −7.89 | >−4.00 | −4.75 | −4.92 | — | >−4.00 | −4.10 | −4.43 | — |
| UO-31 | −4.06 | <−8.00 | −7.17 | −6.09 | >−4.00 | −5.67 | −5.65 | — | >−4.00 | −5.21 | −5.16 | — |
| Prostate Cancer | | | | | | | | | | | | |
| PC4 | −4.17 | <−8.00 | <−8.00 | −10.85 | >−4.00 | −4.94 | −4.95 | >−4.00 | >−4.00 | >−4.00 | −4.37 | >−4.00 |
| DU-145 | — | −4.92 | −4.94 | −9.38 | — | −4.59 | −4.62 | >−4.00 | — | −4.25 | −4.30 | — |
| Breast Cancer | | | | | | | | | | | | |
| MCF7 | >−4.00 | — | −7.03 | −11.69 | >−4.00 | −4.79 | −4.94 | −4.05 | >−4.00 | −4.27 | −4.40 | >−4.00 |
| MCF7/ADR- | — | −6.61 | −4.96 | −8.48 | — | >−4.00 | −4.58 | −4.00 | — | >−4.00 | −4.20 | >−4.00 |

TABLE I-continued

| Panel/ | | Log$_{10}$ GI$_{50}$ | | | | Log$_{10}$ TGI | | | | Log$_{10}$ LC$_{50}$ | | |
| --- | --- | --- | --- | --- | --- | --- | --- | --- | --- | --- | --- | --- |
| | | HDQHS Dimer | | Pacli- | | HDQHS Dimer | | Pacli- | | HDQHS Dimer | | Pacli- |
| Cell line | QHS | β, β | α, β | taxel | QHS | β, β | α, β | taxel | QHS | β, β | α, β | taxel |
| RES | | | | | | | | | | | | |
| MDA-MB-231/ATCC | −4.20 | −5.50 | −5.07 | −8.54 | >−4.00 | −4.81 | −4.66 | −4.84 | >−4.00 | −4.37 | −4.30 | −4.29 |
| HS 578T | >−4.00 | <−8.00 | −7.09 | — | >−4.00 | −6.42 | −5.10 | — | >−4.00 | −4.28 | −4.23 | — |
| MDA-MB-435 | — | — | −5.92 | <−13.00 | — | −4.82 | −4.77 | — | — | −4.34 | −4.35 | — |
| MDA-N | >−4.00 | <−8.00 | −6.53 | <−13.00 | >−4.00 | −4.78 | −4.82 | — | >−4.00 | −4.10 | −4.31 | — |
| BT-549 | −4.06 | — | — | −9.31 | >−4.00 | — | — | −6.32 | >−4.00 | — | — | >−4.00 |
| T-47D | — | <−8.00 | <−8.00 | −9.81 | >−4.00 | — | −4.88 | −4.05 | >−4.00 | >−4.00 | >−4.00 | >−4.00 |
| Mean | −4.07 | −6.56 | −6.15 | −10.15 | −4.00 | −4.92 | −4.95 | −4.54 | −4.00 | −4.25 | −4.38 | −4.06 |
| Range | 0.73 | 3.35 | 3.21 | 8.00 | 0.06 | 4.00 | 3.53 | 7.20 | 0.00 | 1.33 | 3.56 | 0.45 |

Figure 1A:
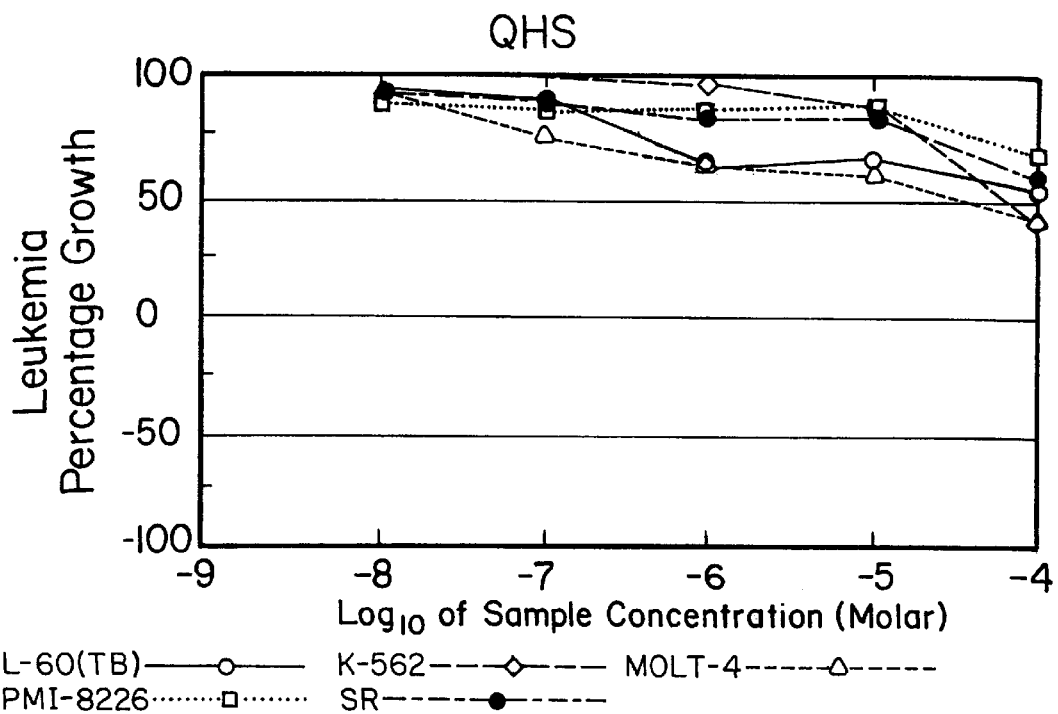
Figure 1B:
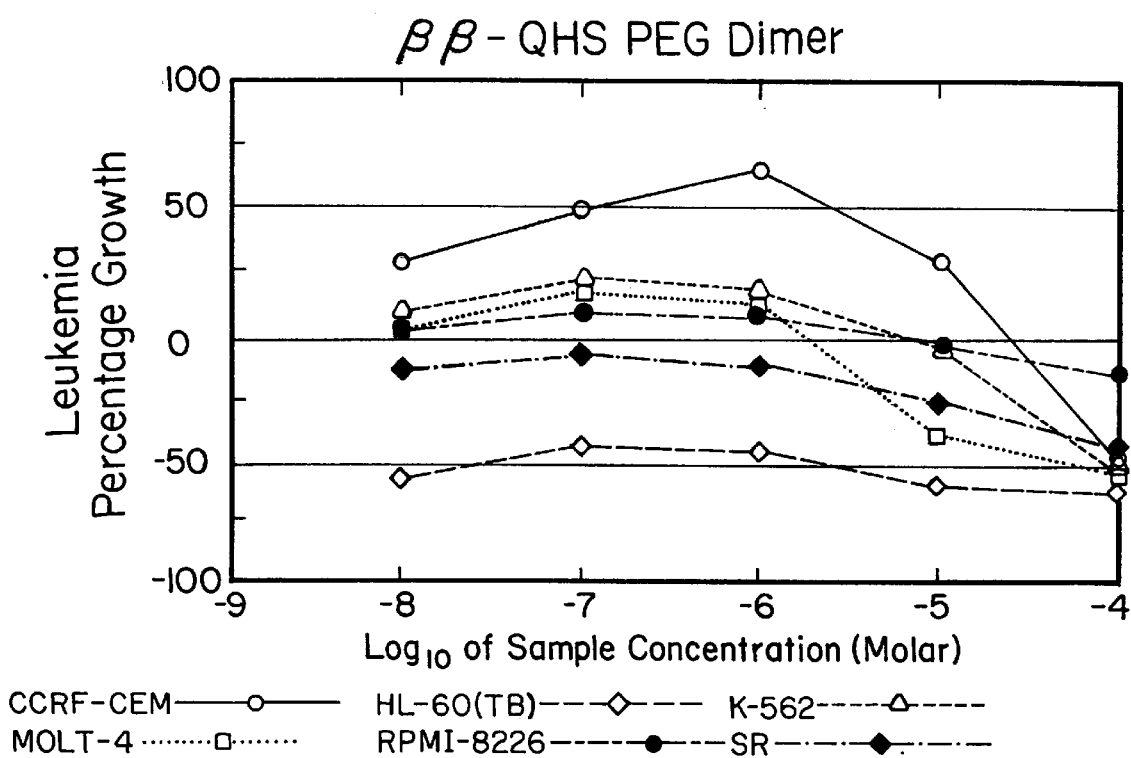
Figure 1C:
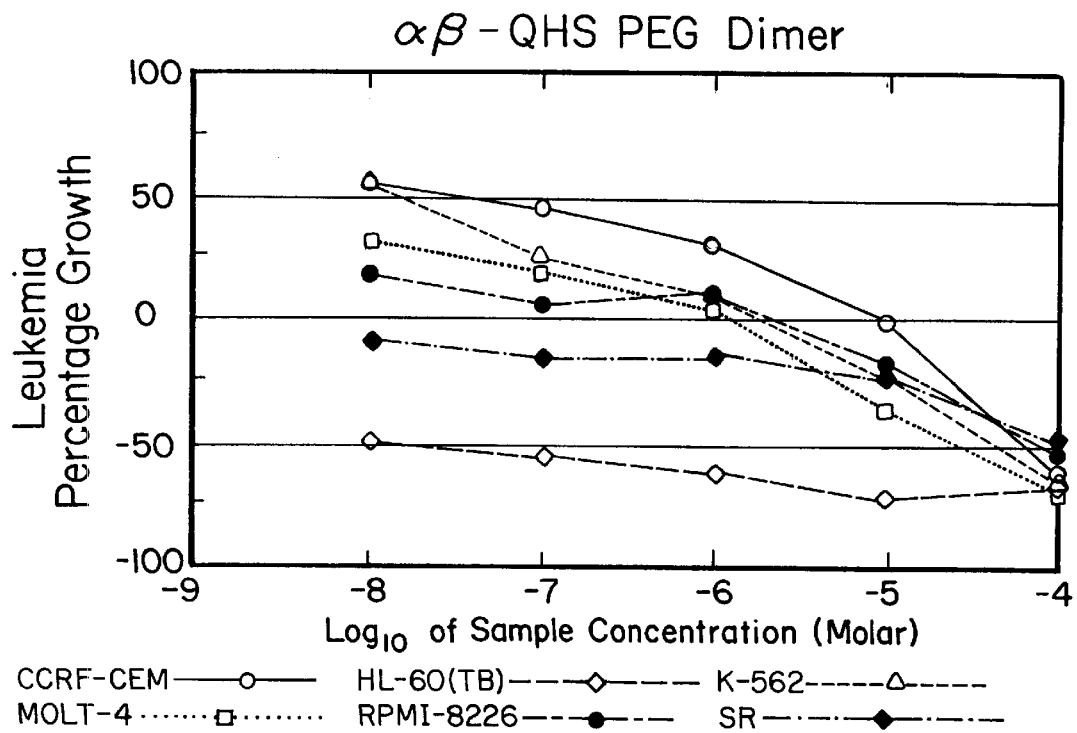
Figure 1D:
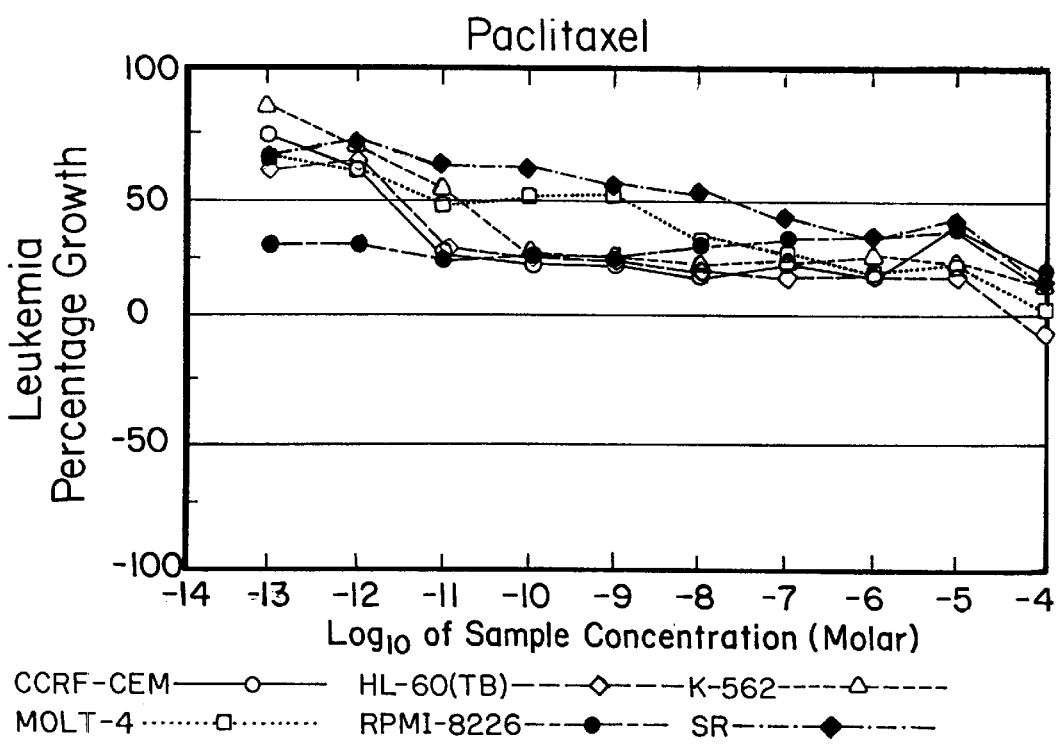

The HDQHS dimers of the present invention in most instances are as potent and in some instances more potent than paclitaxel. The data in Table 1 is graphically represented in FIGS. 1a, b, c, and d through FIGS. 9a. Dose response curves, shown in the above mentioned Figures, are obtained by exposing various cancer cell lines to compounds having a known concentration ([$\log_{10}$M]), as discussed in detail above, and then plotting the percentage growth of each cell line for each concentration. The drug concentration limits that are tested are between $10^{-4}$ or −4.00M and $10^{-8}$ or −8.00M. The −4.00M value being the high concentration and the −8.00M value being the low concentration. Percentage growth is determined by dividing the number or mass of cells in the test well by the number or mass of cells in a control well. Referring to the leukemia cell line MOLT-4 in FIGS. 1a, 1b, 1c and 1d the first comparison that is made between QHS, the QHS dimers of the present invention (β, β-QHS Dimer and α, β-QHS dimer) and paclitaxel are the drug concentrations which are necessary to inhibit growth, graphically represented in FIGS. 1a, 1b, 1c, and 1d as the concentration necessary to achieve the percentage growth value of +50. As discussed previously, the five drug dilutions routinely tested range from $10^{-4}$ to $10^{-8}$ molar. Therefore, concentrations less than or greater than $10^{-8}$ and $10^{-4}$ molar, respectively, that are required to achieve a desired result are not determined. Referring now to FIG. 1a, some concentration of QHS that is greater than $10^{-4}$ molar is necessary to achieve primary growth inhibition. Referring to the β, β-QHS PEG dimer and α, β-QHS PEG dimer dose response curves in FIGS. 1b and 1c, respectively, the leukemia cell line MOLT-4 displays primary growth inhibition at drug concentrations that are less than $10^{-8}$M. The same can be said for paclitaxel, see FIG. 1d; however, the lower concentrations have been determined for this drug and the concentration at which primary growth inhibition occurs using paclitaxel is at −11.07 molar. The drug concentration at which QHS is considered cytostasis, i.e. percentage growth is equal to 0, is at some concentration greater than −4.00 molar. The β, β-QHS PEG dimers and α, β-QHS PEG dimers reach cytostasis at drug concentrations of −5.80M and −5.93M, respectfully, while the paclitaxel concentration necessary to achieve cytostasis is some value greater than −4.00 molar. Cytotoxicity, i.e., the concentration for which the percentage growth is equal to −50, occurs at a concentration greater than −4.00M for QHS, −4.55M for the β, β-QHS PEG dimer, −4.73M for the α, β-QHS PEG dimer, and a concentration greater than −4.00M for paclitaxel.

The potency of QHS dimers of the present invention as compared to QHS and paclitaxel varies from cell line to cell line. However, the mean values for each drug are presented at the end of Table 1 and QHS dimers of the present invention were more potent than QHS and equivalent to and in many instances greater than that for paclitaxel.

The DHQHS condensation by-product disclosed by M. Cao et al., and tested by D. L. Klayman and H. J. Woerdenbag, discussed previously, was approximately twenty-two times more potent at causing 50% growth inhibition in one cell line than QHS. With respect to the drug concentrations causing 50% growth inhibition, the QHS dimers were at least 100 times more potent than QHS. When interpreting the mean values, it is important to take into consideration that drug concentrations less than $10^{-8}$M and greater then $10^{-4}$M were not collected, this factor is reflected in the range.

Figure 2A:
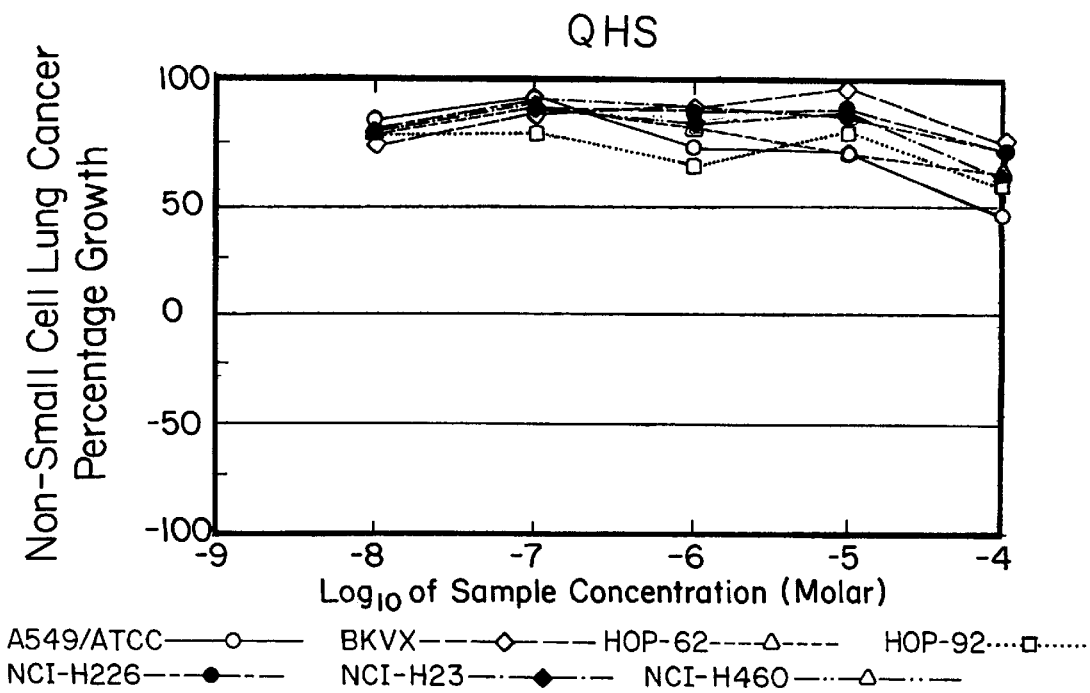
Figure 2B:
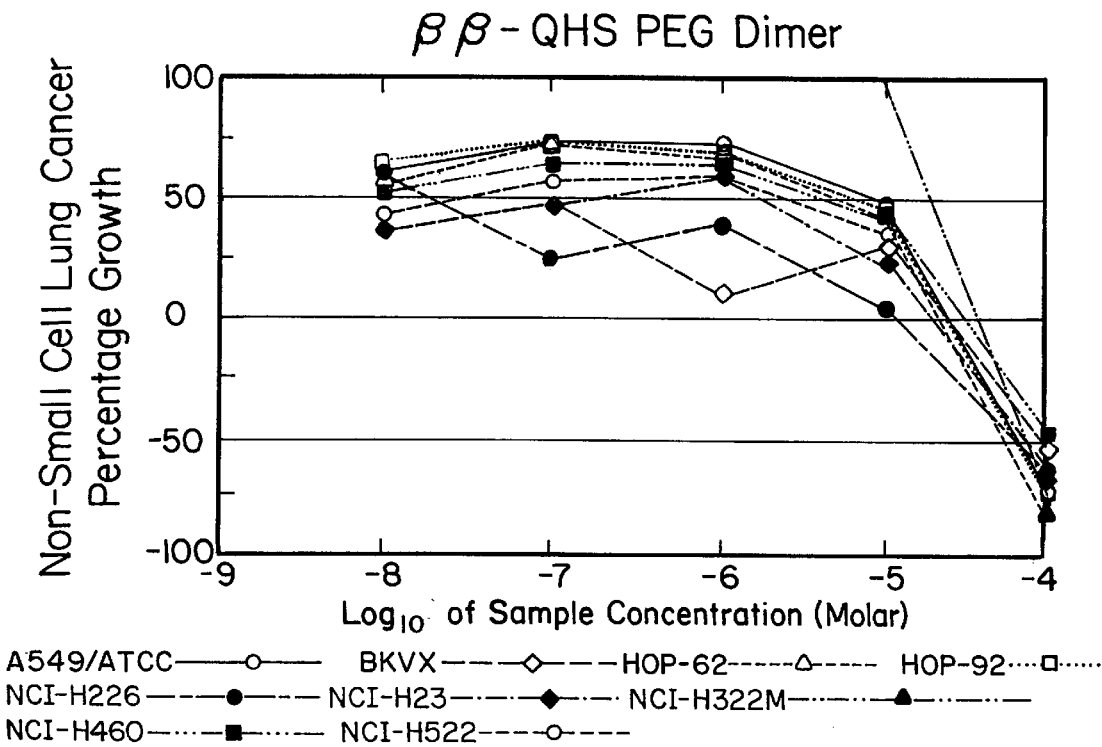
Figure 2C:
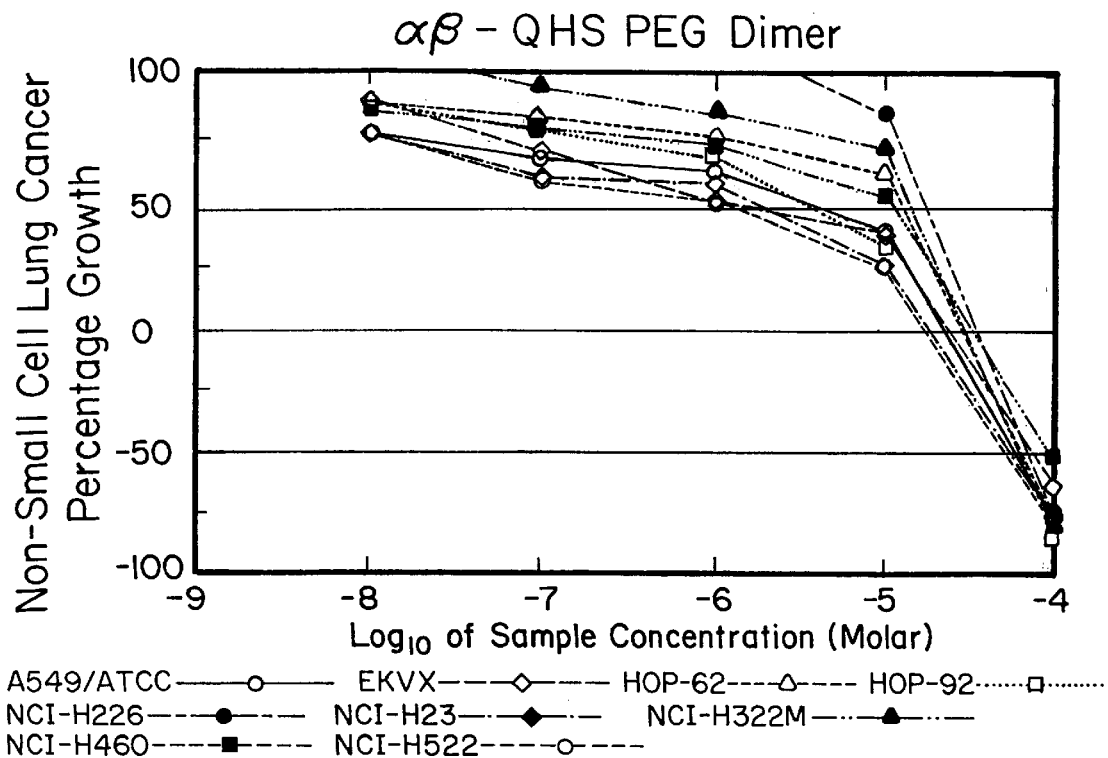
Figure 2D:
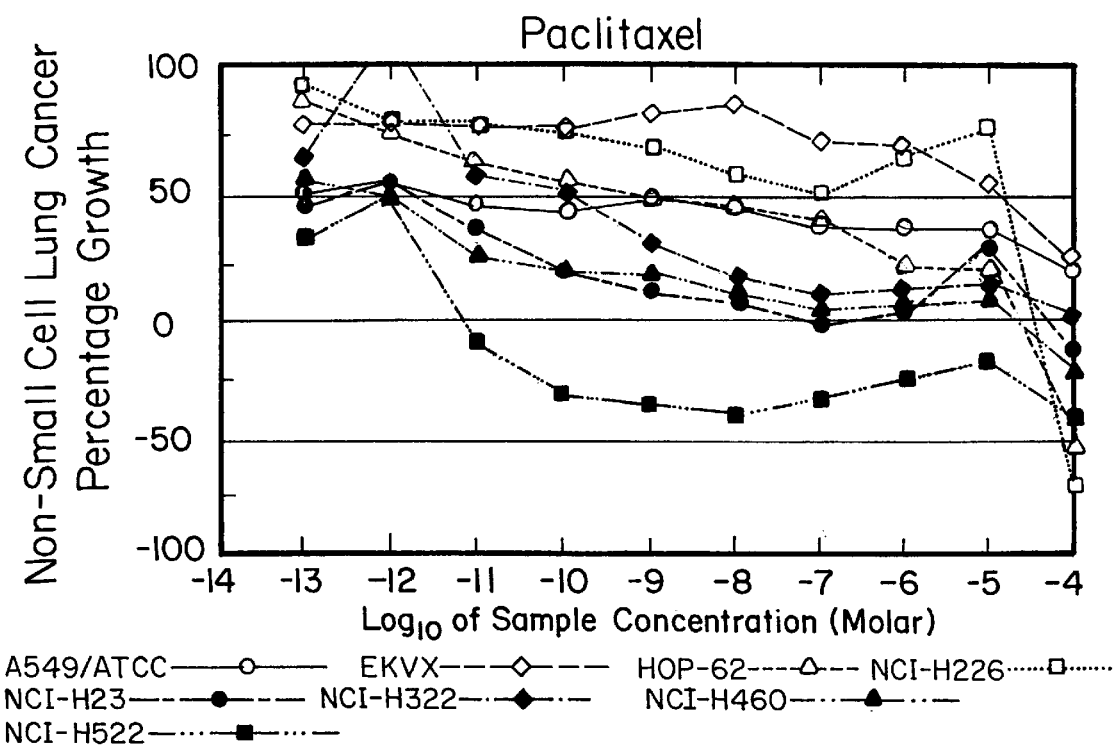

For a further comparison on the effects of the QHS PEG dimers of the present invention on various cancer cell lines versus the effects of QHS and paclitaxel on the same cell lines see FIGS. 2a, b, c and d for non-small cell lung cancer cell lines, FIGS. 3a, b, c, and d for colon cancer cell lines, FIGS. 4a, b, c and d for CNS cancer cell lines, FIGS. 5a, b, c, and d for melanoma cancer cell lines, FIGS. 6a, b, c, and d for ovarian cancer cell lines FIGS. 7a, b, c, and d for renal cancer cell lines, FIGS. 8a, b, c, and d for prostate cancer cell lines and FIGS. 9a, b, c, and d for breast cancer cell lines.

In determining the mode of action by which a compound exerts its cytotoxic effect the National Cancer Institute utilizes the Pearson Correlation Coefficient to provide indications of the probable mode of action. When comparing the dose response profile information to the established chemotherapy drugs with known modes of action, a Pearson Correlation Coefficient of >0.6 indicates a high likelihood of a mode of action which is similar to the comparison compound. A correlation coefficient of <0.6, when compared to the bank of known drugs, is thought to be indicative of the possibility of an unknown mechanism. The following Table II shows the Pearson Correlation Coefficient for the artemisinin dimer of the present invention at GI$_{50}$, TGI and LC$_{50}$ at a $\log_{10}$ [−4.00M].

TABLE II

| Comparison Correlation | Chemical Name | Pearson Correlation Coefficient |
| --- | --- | --- |
| GI$_{50}$ | Carboxyphthalato Platinium | 0.458 |
| | Tetraplatin | 0.449 |
| | 8-Cl CYC AMP | 0.432 |

TABLE II-continued

| Comparison Correlation | Chemical Name | Pearson Correlation Coefficient |
|---|---|---|
| | Diglycoaldehyde | 0.428 |
| | Trimethyltrimethyiolmelamine | 0.388 |
| | DUP785 (Brequinar) | 0.381 |
| | Rifamycin SV | 0.376 |
| | 3-Deazauridine | 0.374 |
| | Hydrazine Sulfate | 0.361 |
| | Caracemide | 0.346 |
| | Aclacinomycin A | 0.355 |
| TGI | Hydroxyurea | 0.745* |
| | Bis-Pyridocarbazolium DMS | 0.558 |
| | Glyoaxalic Alkylat. Deriv. | 0.528 |
| | 6-Mercaptopurine | 0.440 |
| | Diglycoaldehyde | 0.422 |
| | Macbetin II | 0.419 |
| | Dihydro-5-Azacytidine | 0.390 |
| | Caracemide | 0.368 |
| | BCNU | 0.361 |
| | Merbarone | 0.356 |
| | AMSA | 0.347 |
| $LC_{50}$ | Flavone Acetic Acid | 0.707* |
| | DUP785 (brequinar) | 0.546 |
| | Triethylenemelamine | 0.475 |
| | Hepsulfam | 0.474 |
| | Dihydro-Lenperone | 0.470 |
| | Topotecan | 0.463 |
| | Cytembena | 0.450 |
| | Thio-Tepa | 0.433 |
| | Tetrocarcin A Sodium Salt | 0.425 |
| | Pancratiastatin | 0.413 |
| | CCNU | 0.403 |

*NCI indicates these values are not relevant

As a result of the Pearson Correlation Coefficient being less than 0.6 the NCI has referred the artemisinin dimers of the present invention for further in vivo testing. Of the 40,000 compounds tested by NCI over the past two years only 160 compounds have been chosen for in vivo testing.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art.

All temperatures are understood to be in Centigrade (° C.) when not specified. The nuclear magnetic resonance (NMR) spectral characteristics refer to chemical shifts δ expressed in parts per million (ppm) versus tetramethylsilane (TMS) as reference standard. $^1$H and $^{13}$C NMR spectra were recorded on a JEOL Eclipse-400 instrument. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiple (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethysulfoxide), $D_2O$ deuterated water), $CDCl_3$ (deuterochloroform) and other conventional deuterated solvents. The chemical shifts are expressed in ppm relative to the reference of $CDCl_3$ or DMSO. Deuterated solvents were purchased from Aldrich Chemical Co. The infrared (IR) spectral description was measured on a KVB Analect Diamond-20 FT-IR Spectrometer featuring a Laser Precision XAD-Plus Microscope. Electrospray mass spectra were obtained from a VG Platform HPLC-MASS Spectrometer. TLC plates of silica gel 60F254 were purchased from E. M. Merck and kept in a closed container over Drierite® prior to use. Melting points were measured on a MEL-TEMP II apparatus equipped with a digital Barnant 100 Thermocouple Thermometer and are uncorrected. HPLC was performed on a Hitachi chromatographic spectrometer (L-6200A Intelligent Pump, D-6000 Interface, L-4000 UV Detector and AS-4000 Intelligent Auto Sampler). Combination of $CH_3CN$ and $H_2O$ in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely listed by way of example and is not intended to limit the invention.

EXAMPLE I

Small Scale Preparation of DHQHS-Trimethylene Glycol Dimer 116.1 mg (0.409 mmol) of DHQHS and 12 ml (0.03M) of toluene were introduced under a nitrogen atmosphere into a 25 ml round bottomed flask equipped with a magnetic stir bar. 27.8 μl (0.204 mmol, 0.5 eq) of trimethylene glycol was added followed by 12.0 μl (0.098 mmol, 0.24 eq) of $BF_3.Et_2O$ and the mixture was then stirred at room temperature for three hours.

Methylene chloride was then added to the mixture. The reaction mixture presumed to contain DHQHS-PEG dimer was washed twice with water. The organic phase was collected, dried over magnesium sulfate and subsequently filtered. The solvent was removed under reduced pressure to obtain a colorless oil as crude product. The crude product was purified by flash chromatography on silica gel and eluted with 20% ethylacetate/hexane followed by 30% ethylacetate/hexane. The 20% ethylacetate/hexane solution contains trimethylene glycol and other impurities. The 30% ethylacetate/hexane solution contains the pure mixtures of isomers of DHQHS-PEG dimers and monomers. The selected fractions were evaporated to dryness with a rotary evaporation under reduced pressure. 32.2 mg of starting material was recovered resulting in a 27.7% yield. The DHQH-PEG dimer was isolated in 32.8% yield (15.4% ββ dimer, 9.0% α β dimer, and 8.4% α α dimer). The DHQH-PEG monomer (mixture of α+β isomers) was obtained in a 19.7% yield. The proton nuclear magnetic resonance spectrum of β, β dimer (400 MHz; deuterated chloroform; chemical shift in ppm; coupling constants J in Hz): $^1$H NMR (400 MHz, $CDCl_3$) δ 0.8564 (d, J=7.32 Hz, 3H, C-13), 0.8940 (d, J=6.24 Hz, 3H, C-14), 1.19 (m, 1H), 1.28 (m, 1H), 1.38 (s, 3H, C-15), 1.39–1.84 (m, 7H), 1.98 (m, 1H), 2.30 (td, J=13.56, 4.04 Hz, 1H) 2.55 (m, 1H, C-11), 3.56 (m, 4H), 3.88 (m, 2H), 4.76 (d, J=3.32 Hz, 1H, C-12), 5.36 (s, 1H, C-5); $^{13}$C NMR (100 MHz, $CDCl_3$) δ 13.04, 20.43, 24.45 24.75, 26.22, 30.91, 34.74, 36.47, 37.47, 44.51, 52.62, 67.44, 70.59, 70.63, 81.13, 87.87, 102.09, 104.02; MS (Electrospray) m/e 700.3 $(M+NH4)^+$.

EXAMPLE II

Large Scale Preparation of DHQHS-Trimethylene Glycol Dimer 593.3 mg (2.11 mmol) of DHQHS and 60 ml (0.04M) of toluene were introduced under a nitrogen atmosphere into a 25 ml round bottomed flask equipped with a magnetic stir bar. 144 µl (1.06 mmol, 0.5 eq) of trimethylene glycol was added followed by 64 µl (0.53 mmol, 0.25 eq) of $BF_3.Et_2O$ and the mixture was then stirred at room temperature for three hours.

Methylene chloride was then added to the mixture. The reaction mixture presumed to contain DHQHS-PEG dimer was washed with water. The organic phase was collected, dried over magnesium sulfate and subsequently filtered. The solvent was removed under reduced pressure to obtain 731.3 mg colorless oil as crude product corresponding to a crude yield of 98.1%. The crude product was purified by flash chromatography on silica gel (60 Å) and eluted with a gradient elution of 20–50% ethylacetate/hexane. The DHQHS-PEG dimer was obtained as oil (348.2 mg, 47.7%). 228.0 mg of the β β dimer (30.6%), 97.3 mg of the α β dimer (13.1%) and 29.9 mg of the a at dimer (4.0%) were recovered. 136.8 mg of the monomer (α+β, 15.2%) and 25.1% of the starting material were also recovered. The $^1$H NMR, $^{13}$C NMR, and MS data are identical to that in Example I.

EXAMPLE III

Small Scale Preparation of DHQHS-Diethylene Glycol Dimer 100.3 mg (0.35 mmol) of DHQHS and 12 ml (0.03M) of toluene were introduced under a nitrogen atmosphere into a 25 ml round bottomed flask equipped with a magnetic stir bar. 17.0 µl (0.18 mmol, 0.5 eq) of diethylene glycol was added followed by 11.0 µl (0.09 mmol, 0.25 eq) of $BF_3.Et_2O$ and the mixture was ten stirred at room temperature for three hours.

Methylene chloride was then added to the mixture. The reaction mixture presumed to contain diethylene glycol-DHQHS dimer was washed twice with water. The organic phase was collected, dried over magnesium sulfate and subsequently filtered. The crude product was purified by flash column chromatography on silica gel and eluted with a gradient solvent system (15–80% ethylacetate/hexane). The selected fractions were evaporated to dryness with a rotary evaporation under reduced pressure. 6.2 mg of DQHS was recovered. 45.3 mg of dimers (29.8 mg β β dimer, 12.3 mg α β dimer, and 3.2 mg α α dimer) were obtained as desired product in 39.5% yield. The proton nuclear magnetic resonance spectrum for the β β dimer (400 MHz; deuterated chloroform; chemical shift in ppm; coupling constants J in Hz): $^1$H NMR (400 MHz, $CDCl_3$) δ 5.41 (s, 1H), 4.82 (d, J=3.28 Hz, 1H), 3.94 (m, 1H), 3.53–3.67 (m, 3H), 2.60 (m, 1H), 2.35 (m, 1M, 2.00 (m, 11), 1.70–1.90 (m, 3H ), 1.59 (m, 2H), 1.47 (m, 1H), 1.42 (s, 3H), 1.20–1.40 (m, 3H ), 0.91 (d, J=6.20 Hz, 3H ), 0.87 (d, J=7.32 Hz, 3H); MS (electrospray) m/e 656.1 $(M+NH4)^+$.

EXAMPLE IV

Large Scale Preparation of DHQHS-Diethylene Glycol Dimer 501.8 mg (1.78 mmol) of DHQHS and 60 ml (0.03M) of toluene were introduced under a nitrogen atmosphere into a 25 ml round bottomed flask equipped with a magnetic stir bar. 84 µl (0.88 mmol, 0.5 eq) of diethylene glycol was added followed by 54 µl (0.44 mmol, 0.25 eq) of $BF_3 . Et_2O$ and the mixture was then stirred at room temperature for three hours.

Methylene chloride was then added to the mixture. The reaction mixture presumed to contain Diethylene glycol-DHQHS dimer was washed with water. The organic phase was collected, dried over magnesium sulfate and subsequently filtered. The crude product was purified by flash column chromatography on silica gel and eluted with a gradient solvent system of 15–75% ethylacetate/hexane. Less than 10 mg of DHQHS was recovered while 334.0 mg of dimers (238.3 mg β β dimers, 8.3 mg α β+β β dimers, 79.0 mg α β dimer, and 8.4 mg α α dimer) were obtained as desired product in 59.5% yield. The $^1$H NMR and MS data of this dimer is identical to the one in Example III.

EXAMPLE V

Small Scale Preparation of DHQHS-Hexaethylene Glycol Dimer 100.9 mg (0.36 mmol) of DHQHS and 12 ml (0.03M) of toluene were introduced under a nitrogen atmosphere into a 25 ml round bottomed flask equipped with a magnetic stir bar. 45.0 µl (0.18 mmol, 0.5 eq) of hexaethylene glycol was added followed by 11.0 µl (0.09 mmol, 0.25 eq) of $BF_3.Et_2O$ and the mixture was then stirred at room temperature for three hours.

Methylene chloride was then added to the mixture. The reaction mixture presumed to contain the hexaethylene glycol dimer was washed twice with water. The organic phase was collected, dried over magnesium sulfate and subsequently filtered. Flash column chromatography (silica gel) was used to purify the product with a gradient solvent system (15–95% ethylacetate/hexane). The solvent system was then gradually changed to 5–10% methanol/methylene chloride to recover all products. The selected fractions were evaporated to dryness with a rotary evaporation under reduced pressure. 62.2 mg of starting material was recovered, and 15.7 mg of dimer was isolated in 11.9% yield (9.0 mg β β dimer, 4.0 mg αβ+β β dimers, and 2.7% α β dimer). The proton nuclear magnetic resonance spectrum for the β β dimers (400 MHz; deuterated chloroform; chemical shift in ppm; coupling constants J in Hz): $^1$H NMR (400 MHz, $CDCl_3$) δ 5.41 (s, 1H), 4.82 (d, J=3.32 Hz, 1H), 3.94 (m, 1H), 3.60 (m, 11H), 2.60 (m, 1H), 2.60 (m, 1H), 2.35 (m, 1H), 2.00 (m, 1H), 1.70–1.90 (m, 3H), 1.59 (m, 2H), 1.47 (m, 1H), 1.42 (s, 3H), 1.20–1.40 (m, 3H), 0.91 (d, J=7.32 Hz, 3H), 0.87 (d, J=6.56 Hz, 3H); MS (electrospray) m/e 832.3 $(M+NH4)^+$.

EXAMPLE VI

Large Scale Preparation of DHQHS-Hexaethylene Glycol Dimer 506.2 mg (1.78 mmol) of DHQHS and 60 ml (0.03M) of toluene were introduced under a nitrogen atmosphere into a 25 ml round bottomed flask equipped with a magnetic stir bar. 250 µl (0.89 mmol, 0.5 eq) of hexaethylene glycol was added followed by 55 µl (0.45 mmol, 0.25 eq) of $BF_3.Et_2O$ and the mixture was then stirred at room temperature for three hours.

Methylene chloride was then added to the mixture. The reaction mixture presumed to contain hexaethylene glycol dimer was washed with water. The organic phase was collected, dried over magnesium sulfate and subsequently filtered. The crude product was purified by flash column chromatography on silica gel and eluted with a gradient elution of 15–95% ethylacetate/hexane. The solvent system was then gradually changed to 5–10% methanol/methylene chloride to recover all products. 62.0 mg of starting material was recovered, and 102.5 mg of dimer was isolated in 14.2% yield (67 mg β β dimers, 35.0 mg α β+β β dimers). The analytical results are identical to the dimer in Example V.

The foregoing description is considered as illustrative only of the principals of the invention. Furthermore, since numerous modifications and changes will readily occur to those skilled in the art, it is not desired to limit the invention to the exact compositions and processes shown as described above. Accordingly, all suitable modifications and equivalents may be resorted to falling within the scope of the invention as defined by the claims which follow.

EXAMPLE VII

Preparation of DHQHS-Carbonate Dimer 140.0 mg (0.500 mmol) of DHQHS dissolved in 3.0 ml of a 10% pyridine/methylene chloride solution was introduced into a 25 ml round bottomed flask equipped with a magnetic stir bar. 40.0 mg (0.25 mmol) of 1, 3-phenylenediisocyanate was added and the mixture was then stirred at room temperature overnight.

The solution was concentrated to dryness and the resulting residue was purified by flash column chromatography on silica gel eluted with 10–25% elthylacetate/hexane. The selected fractions were evaporated to dryness with a rotary by rotary evaporation under reduced pressure. 80 mg of 12-carbonate artemisinin dimer was obtained as a white solid resulting in a 50% yield. The proton nuclear magnetic resonance spectrum (400 MHz; deuterated chloroform; chemical shift in ppm; coupling constants J in HZ): $^1$H NMR (400 MHz, CDCL$_3$) δ 0.95 (m, 12H, H-13, H-14), 1.36 (s, 6H, H-15), 2.62 (m, 2H, H-11), 5.50 (s, 2H, H-5), 5.76 (d, J=9.98 Hz, 2H, H-12), 7.14 (s, 1H, Ph-H), 7.34 (m, 3H, Ph—H); 13C NMR (10 MHz, CDCl$_3$) δ 12.2, 20.3, 22.1, 24.7, 25.9, 31.9, 34.2, 36.6, 37.4, 45.4, 51.7, 80.3, 91.5, 93.0, 104.6, 113.8, 129.5, 138.3, 151.9; IR (neat) 3400, 3000, 1750, 1050, cm-1; MS (electrospray) m/e 746 (M+NH$_4$)$^+$.

The embodiments of the invention in which an exclusive property or privilege is claimed are defined as follows:

1. A method for treating cancer, which comprises administering to a patient suffering from said cancer an artemisinin dimer of the formula:

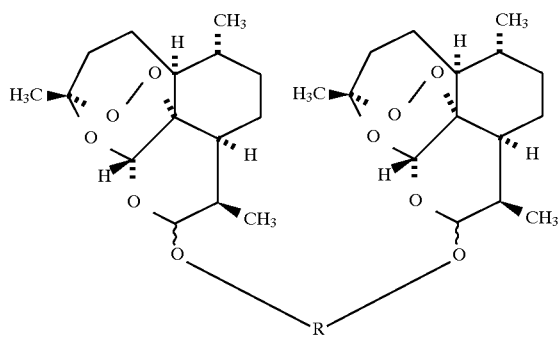

or an isomer thereof where R is a linker.

2. A method according to claim 1, wherein said R is a bivalent halide species, lower alkylene, lower alkenylene, arylene, a bivalent protein, a bivalent atom, —CH$_2$CH$_2$—(ACH$_2$CH$_2$)$_n$— where A is O, S or NY where Y is H or alkyl and n is 0–20 and —X—Z—X— wherein X is a bivalent ester, carbamate or carbonate species and Z is arylene, polyethylene glycol (PEG), lower alkylene, or lower alkenylene.

3. A method according to claim 1, wherein said R is (CH$_2$CH$_2$O)$_n$ and n is 1–20.

4. A method according to claim 3, where n is 2.

5. A method according to claim 3, where n is 3.

6. A method according to claim 3, where n is 6.

7. A method for treating cancer, which comprises administering to a patient suffering from said cancer an artemisinin dimer of formula:

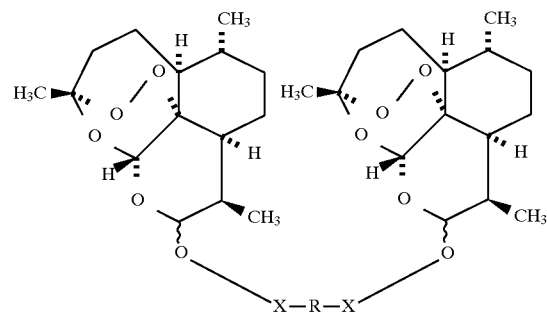

or an isomer thereof wherein X is a bivalent ester, carbonate, or carbamate species carbonyl, and R is alkylene, alkenylene, arylene, a bivalent halide species, or polyethylene glycol.

8. A method according to claim 7, where X is

and R is —(CH$_2$)$_n$— where n is 1–20.

9. A method according to claim 8, where n is 4.

10. A method according to claim 7, where X is

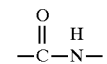

and R is —(CH$_w$)$_n$— where n is 1–20.

11. A method according to claim 10, where n is 6.

12. A method according to claim 10, where R is a phenylene.

13. A method according to claim 7, where X is

and R is —(CH$_2$)$_n$— where n is 1–20.

14. A method for treating cancer, which comprises administering to a patient suffering from said cancer an artemisinin dimer of the formula:

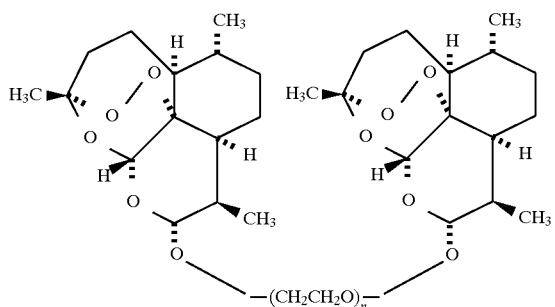

or an isomer thereof, wherein n is 1–20.

15. A method according to claim 14, where n is 2.

16. A method according to claim 14, where n is 3.

17. A method according to claim 14, where n is 6.

18. A method for treating cancer, which comprises administering to a patient suffering from said cancer an artemisinin dimer of the formula:

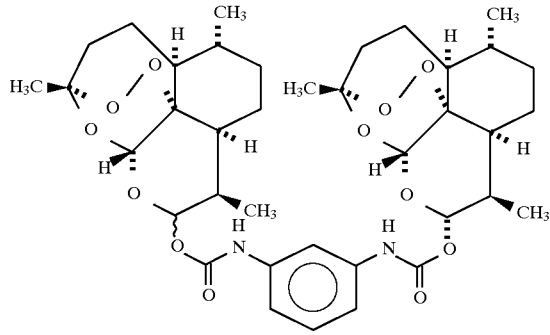

or an isomer thereof.

19. A method according to claim 1, wherein said cancer is selected from the group of cancers consisting of leukemia, non-small-cell lung cancer, colon cancer, central nervous system cancer, melanoma, ovarian cancer, renal cancer, prostate cancer, and breast cancer.

20. A method according to claim 7, wherein said cancer is selected from the group of cancers consisting of leukemia, non-small-cell lung cancer, colon cancer, central nervous system cancer, melanoma, ovarian cancer, renal cancer, prostate cancer, and breast cancer.

21. A method according to claim 14, wherein said cancer is selected from the group of cancers consisting of leukemia, non-small-cell lung cancer, colon cancer, central nervous system cancer, melanoma, ovarian cancer, renal cancer, prostate cancer, and breast cancer.

22. A method according to claim 18, wherein said cancer is selected from the group of cancers consisting of leukemia, non-small-cell lung cancer, colon cancer, central nervous system cancer, melanoma, ovarian cancer, renal cancer, prostate cancer, and breast cancer.

* * * * *